U S 0 0 5 8 1 1 4 0 9 A

US005811409A

United States Patent [19]
Heerze et al.

[11] Patent Number: 5,811,409
[45] Date of Patent: Sep. 22, 1998

[54] TREATMENT OF CHOLERA

[75] Inventors: Louis D. Heerze; Glen D. Armstrong, both of Edmonton, Canada

[73] Assignee: Synsorb Biotech, Inc., Calgary, Canada

[21] Appl. No.: 460,893

[22] Filed: Jun. 5, 1995

[51] Int. Cl.$^6$ ............................................. A61K 31/70
[52] U.S. Cl. ........................... 514/54; 514/23; 514/53; 424/194.1; 436/94
[58] Field of Search ............................. 514/23, 53, 54; 427/194.1; 436/94

[56] References Cited

U.S. PATENT DOCUMENTS

| 4,137,401 | 1/1979 | Lemieux et al. | 536/116 |
|---|---|---|---|
| 4,238,473 | 12/1980 | Lemieux et al. | 536/1.11 |
| 4,362,720 | 12/1982 | Lemieux et al. | 514/25 |
| 5,079,353 | 1/1992 | Ratcliffe et al. | 536/53 |
| 5,484,773 | 1/1996 | Heerze | 514/23 |

FOREIGN PATENT DOCUMENTS

| 77 28163 | 9/1977 | France . |
|---|---|---|
| PCT/FR80/ 00037 | 3/1980 | WIPO . |
| PCT/US92/ 08929 | 10/1992 | WIPO . |

OTHER PUBLICATIONS

Tayot, et al., Chemical Abstracts, vol. 93, No. 1, Jul. 7, 1980.

Abbas, S.A. et al., "Tumor–Associated Oligosaccharides I: Synthesis of Sialyl–Lewis$^a$ Antigenic Determinant" *Sialic Acids, Proc. Japan–German Symp. Berlin*, pp. 22–23 (1988).

Amvam–Zollo, P. et al., "Streptococcus pneumoniae Type XIV Polysaccharide: Synthesis of a Repeating Branched Tetrasaccharide with Dioxa–Type Spacer–Arms" *Carbohydrate Research* 150: 199–212 (1986).

Armstrong, G.D. et al., "Investigation of shiga–like toxin binding to chemically synthesized oligosaccharide sequences" *J. Infect. Dis.* 164: 1160–7 (1991).

Chernyak, A.Y. et al., "A New Type of Carbohydrate–Containing Synthetic Antigen: Synthesis of Carbohydrate–Containing Polyacrylamide Copolymers having the Specificity of 0:3 and 0:4 Factors of Salmonella" *Carbohydrate Research*, 128: 269–282 (1984).

Cox, D., et al. "A New Synthesis of 4–0–α–D–Galactopyranosyl–D–Galacto–Pyranose" *Carbohy. Res.* 62: 245–252 (1978).

Dahmén, J. et al., "2–Bromoethyl glycosides: applications in the synthesis of spacer–arm glycosides" *Carbohydrate Research* 118: 292–301 (1983).

Dahmén, J., et al., "Synthesis of space arm, lipid, and ethyl glycosides of the trisaccharide portion [α–D–Gal–(1–4)–β–D–Gal(1–4)–β–D–Glc] of the blood group p$^k$ antigen: preparation of neoglycoproteins" *Carbohydrate Research* 127: 15–25 (1984).

Eidels, L., et al., Membrane receptors for bacterial toxins, Microbiology Reviews, 47:596–620 (1983).

Ekborg, G. et al., "Synthesis of Three Disaccharides for the Preparation of Immunogens bearing Immunodeterminants Known to Occur on Glycoproteins" *Carbohydrate Research* 110: 55–67 (1982).

Fernandez–Santana, V. et al., "Glycosides of Monoallyl Diethylene Glycol. A New type of Spacer group for Synthetic Oligosaccharides" *J. Carbohydrate Chemistry*, 8(3): 531–537 (1989).

Fishman, P. H. et al., "Gangliosides as Receptors for Bacterial Enterotoxins" *Advances in Lipid Research* 25: 165–187 (1993).

Fügedi, P. et al., "Thioglycosides as Glycosylating Agents in Oligosaccharide Synthesis" *Glycoconjugate J.* 4: 97–108 (1987).

Fukuda et al Comparison of the carbohydrate–binding specificities of cholera toxin and *Escherichia coli* heat–labile enterotoxins LTh–I, LTh–IIa, and LTh–IIb Infect. Immun. 56: 1748–1753(1988).

Garegg, P. J. et al., "A Synthesis of 8–Methoxycarbonyloct–1–yl O–α–D–Galactopyranosyl–(1–3)–0–β–D–Galactopyranosyl–(1–4)–2–Acetamido–2–Deoxy–β–D–Glucopyranoside" *Carbohy. Res.* 136: 207–213 (1985).

Garegg, P. J. et al., "Synthesis of 6– and 6'–deoxy derivatives of methyl 4–0–α–D–galactopyranosyl–β–D–galacto pyranoside for studies of inhibition of pyelonephritogenic fimbriated *E. coli* adhesion to urinary epithelium–cell surfaces" *Carbohy. Res.* 137: 270–275 (1985).

Heerze, L.D. et al., "Oligosaccharide sequences attached to an inert support (SYNSORB) as potential therapy for antibiotic–associated diarrhea and pseudomembranous colitis" *J. Infect. Dis.* 169: 1291–1296 (1994).

Jacquinet, J. C. et al., "Synthesis of Blood–group Substances, Part 11. Synthesis of the Trisaccharide O–α–D–Galactopyranosyl–(1–3)–0–β–D–galactopyranosyl–(1–4)–2–acetamido–2–deoxy–D–glucopyranose" *J.C.S. Perkin* I: 326–330 (1981).

Kameyama, A. et al., "Total synthesis of sialyl Lewis X" *Carbohydrate Res.* 209: c1–c4 (1991).

Kaper, J.B., "Cholera", *Clin.Microb.Rev.*, 8:48–86 (1995).

Koike, K. et al., "Total Synthesis of Globotriaosyl–E and Z–Ceramides and Isoglobotriaosyl–E–Ceramide" *Carbohydr. Res.* 163: 189–208 (1987).

Lanne et al., "On the role of the carboxyl group of sialic acid in binding of cholera toxin to the receptor glycosphingolipid, GM1" J. Biochem., 116: 1269–1274 (1994).

Lee, R.T. et al., "Synthesis of 3–(2–Aminoethylthio) PropylGlycosides" *Carbohydrate Research*, 37: 193–201 (1974).

(List continued on next page.)

*Primary Examiner*—Elli Peselev
*Attorney, Agent, or Firm*—Burns, Doane, Swecker & Mathis, L.L.P.

[57] ABSTRACT

This invention relates to treatment of cholera and related conditions using oligosaccharide compositions which bind *V. cholerae* toxin and/or one or more serotypes of the organism *V. cholerae*. More specifically, the invention concerns neutralization and removal of *V. cholerae* toxin and/or organisms from the intestinal tract.

15 Claims, 9 Drawing Sheets

OTHER PUBLICATIONS

Lemieux, R.U. et al., "The properties of a 'synthetic' antigen related to the blood–group Lewis A" *J. Am. Chem. Soc.*, 97: 4076–83 (1975).

Merritt, Ethan A., et al., "Crystal structure of cholera toxin B–pentamer bound to receptor $G_{M1}$ pentasaccharide", Protein Science, 3:166–175 (1994).

Okamoto, K. et al., "Glycosidation of Sialic Acid" *Tetrahedron* 47: 5835–5857 (1990).

Parikh et al., "Ganglioside–agarose and cholera toxin", Meth. Enzymol., 34:610–619(1974).

Paulsen, "Advances in Selective Chemical Syntheses of Complex Oligosaccharides" *Angew. Chem. Int. Ed. Eng.* 21: 155–173 (1982).

Paulsen, H., "Synthese von oligosaccharid–determinanten mit amid–spacer vom typ des T–antigens" *Carbohydr. Res.* 104: 195–219 (1982).

Rana, S.S. et al., "Synthesis of Phenyl 2–Acetamido–2–Deoxy–3–O–α–L–Fucopyranosyl–β–D–Glucopyranoside and Related Compounds" *Carbohydrate Research* 91: 149–157 (1981).

Schaubach, R. et al., "Tumor–Associated Antigen Synthesis: Synthesis of the Gal–α–(1–3)–Gal–β–(1–4)–GlCNAc Epitope. A specific Determinant for Metastatic Progression?" *Liebigs Ann. Chem.*, pp. 607–614 (1991).

Schengrund et al., "Binding of *Vibrio cholera* toxin and heat–labile enterotoxin of *Escherichia coli* to GM1, derivatives of GM1 and nonlipid oligosaccharide polyvalent ligands" *J. Biol. Chem.* 264: 13233–13237 (1989).

Schmidt, "New Methods for the Synthesis of Glycosides and Oligosaccharides—Are There Alternatives to the Koenigs–Knorr Method?" *Angew. Chem. Int. Ed. Eng.* 25: 212–235 (1986).

Spangler, B.D., "Structure and Function of Cholera Toxin and the Related *Escherichia coli* Heat–Labile Enterotoxin" *Microbiological Reviews*, 56(4): 622–647 (1992).

Tayot et al., "Receptor–specific large–scale purification of cholera toxin on silica beads derivatized with lysoGM1 ganglioside", Eur. J. Biochem. 113: 249–58 (1981).

Uesaka et al., "Simple method of purification of *Escherichia coli* heat–labile enterotoxin and cholera toxin using immobilized galactose" *Microb. Path.* 16: 71–76 (1994).

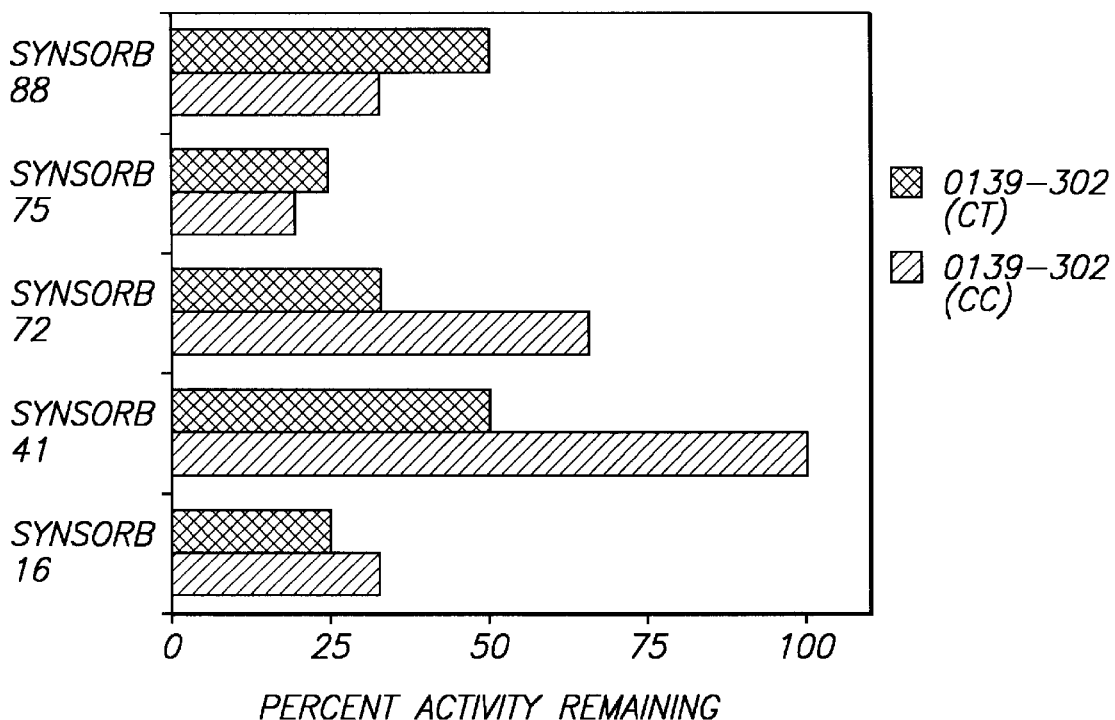
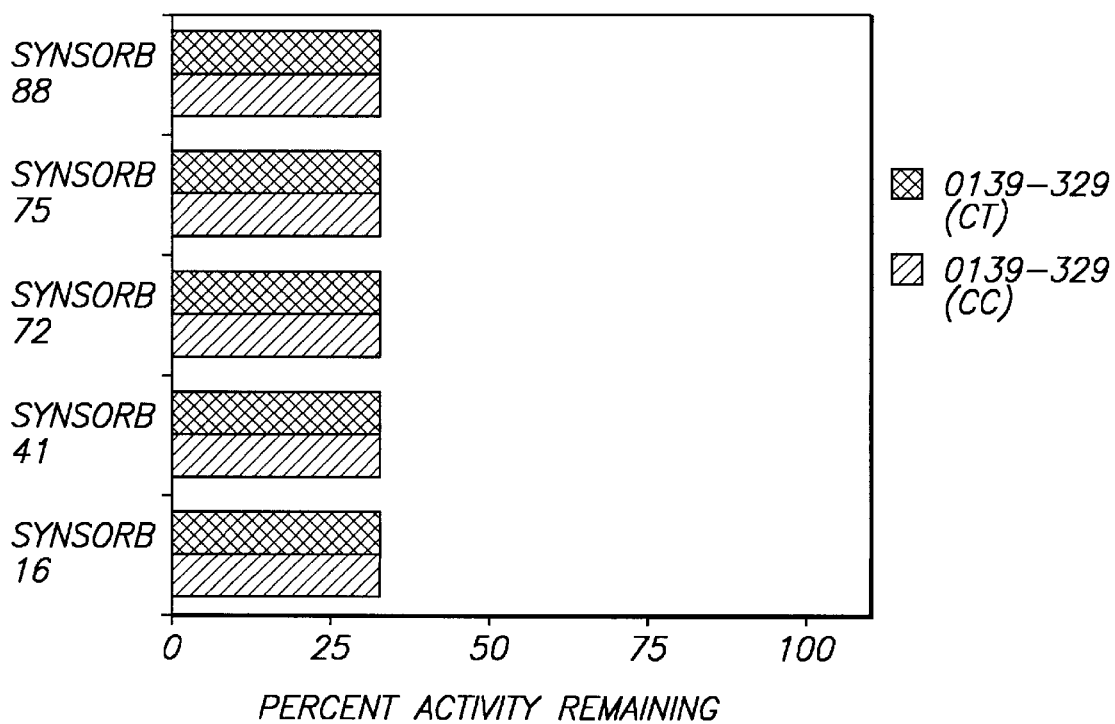
FIG. 3

NEUTRALIZATION OF CC AND CT ACTIVITY FROM 01 El TOR V. CHOLERAE USING SYNSORB

FIG. 4

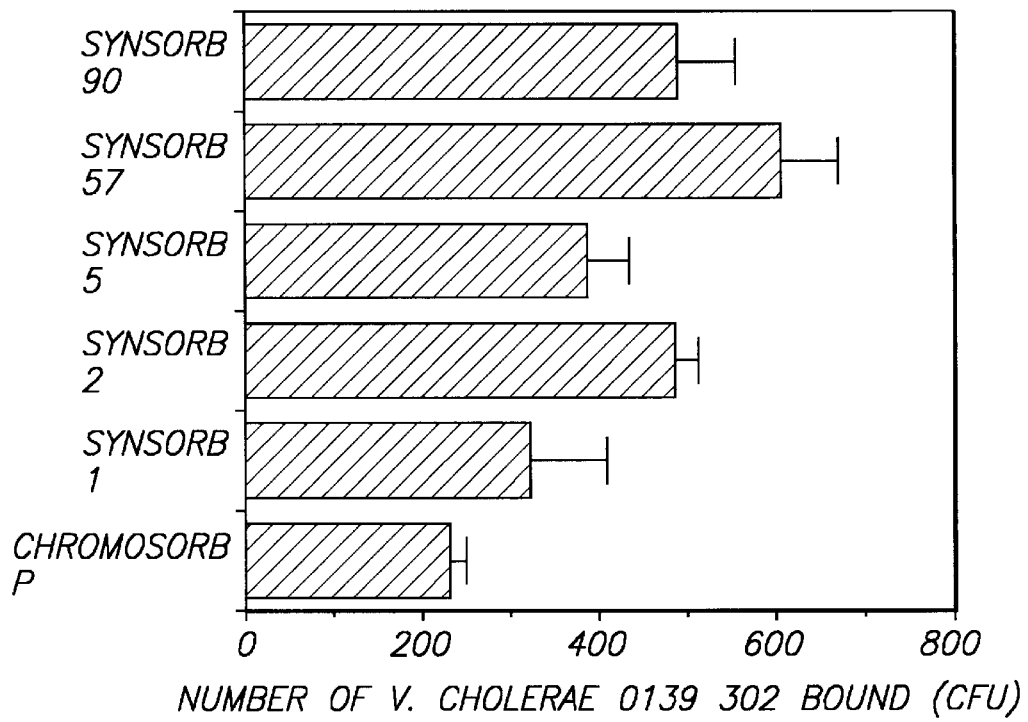
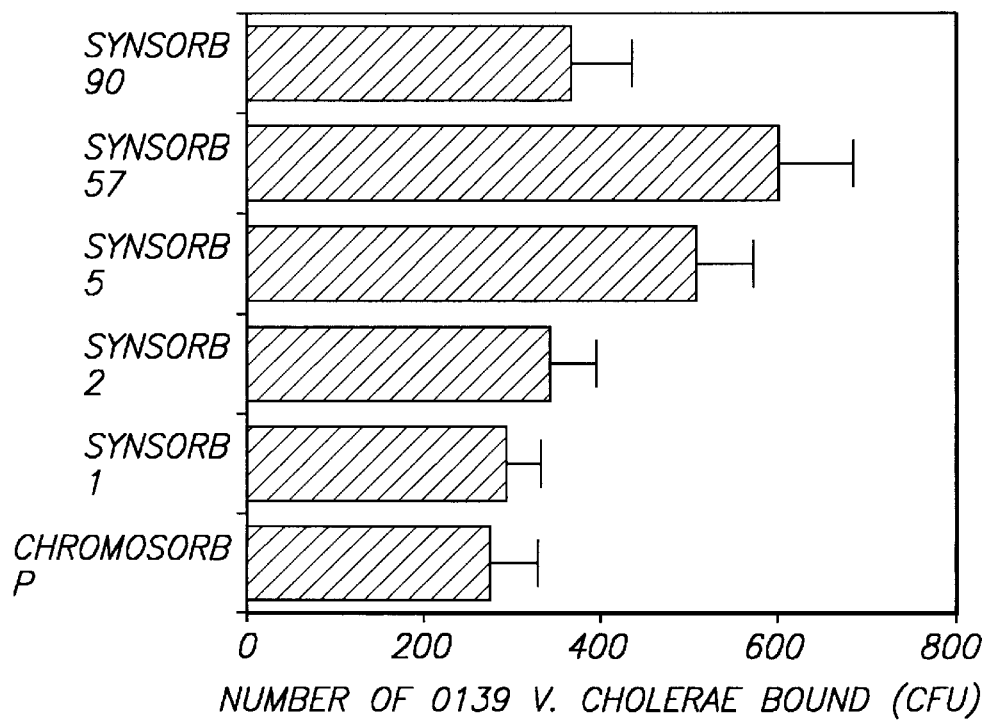
FIG. 9

TREATMENT OF CHOLERA

FIELD OF THE INVENTION

This invention relates to treatment of cholera. More specifically, the invention concerns neutralization and elimination of cholera toxin. This invention also relates to binding and removal of *Vibrio cholerae,* the causative agent of cholera from the intestinal tract.

REFERENCES

The following references are cited in the application as numbers in brackets ([ ]) at the relevant portion of the application.

1. Merritt, Ethan A., et al., "Crystal structure of cholera toxin B-pentamer bound to receptor $G_{M1}$ pentasaccharide", Protein Science, 3:166–175 (1994).

2. Spangler, Brenda D., "Structure and Function of Cholera Toxin and the Related *Escherichia coli* Heat-Labile Enterotoxin", Microbiological Reviews, 56, No. 4:622–647 (1992).

3. Eidels, L., et al., Membrane receptors for bacterial toxins, Microbiology Reviews, 47:596–620 (1983).

4. Fishman, Peter H., et al., "Gangliosides as Receptors for Bacterial Enterotoxins", Advances in Lipid Research, 25:165–187 (1993).

5. Lanne et al., "On the role of the carboxyl group of sialic acid in binding of cholera toxin to the receptor glycosphingolipid, GM1", J. Biochem., 116:1269–1274 (1994).

6. Schengrund et al., "Binding of Vibrio cholera toxin and heat-labile enterotoxin of *Eicherichia coli* to GM1, derivatives of GM1 and nonlipid oligosaccharide polyvalent ligands", J. Biol. Chem., 264:13233–13237 (1989).

7. Fukuda et al., "Comparison of the carbohydrate-binding specificities of cholera toxin and *Escherichia coli* heat-labile enterotoxins LTh-I, LTh-IIa, and LTh-IIb", Infect. Immun., 56:1748–1753(1988).

8. Uesaka et al., "Simple method of purification of *Escherichia coli* heat-labile enterotoxin and cholera toxin using immobilized galactose", Microb. Path., 16: 71–76 (1994).

9. Tayot et al., "Receptor-specific large-scale purification of cholera toxin on silica beads derivatized with lysoGM1 ganglioside", Eur. J. Biochem. 113:249–58 (1981).

10. Parikh et al., "Ganglioside-agarose and cholera toxin", Meth. Enzymol., 34:610–619(1974).

11. Lemieux, R. U., et al., "The properties of a 'synthetic' antigen related to the blood-group Lewis A", J. Am. Chem. Soc., 97:4076–83 (1975).

12. Lemieux, R. U., et al., "Glycoside-Ether-Ester Compounds", U.S. Pat. No. 4,137,401, issued Jan. 30, 1979.

13. Lemieux, R. U., et al., "Artificial Oligosaccharide Antigenic Determinants", U.S. Pat. No. 4,238,473, issued Dec. 9, 1980.

14. Lemieux, R. U., et al., "Synthesis of 2-Amino-2-Deoxyglycoses and 2-Amino-2-Deoxyglycosides from glycals", U.S. Pat. No. 4,362,720, issued Dec. 7, 1982.

15. Cox, D., et al. "A New Synthesis of 4-0-α-D-Galactopyranosyl-D-Galacto-Pyranose", Carbohy. Res., 62: 245–252 (1978).

16. Dahmén, J., et al., "Synthesis of space arm, lipid, and ethyl glycosides of the trisaccharide portion [α-D-Gal-(1–4)-β-D-Gal(1–4)-β-D-Glc] of the blood group $p^k$ antigen: preparation of neoglycoproteins", Carbohydrate Research, 127:15–25 (1984).

17. Garegg, P. J., et al., "A Synthesis of 8-Methoxycarbonyloct-1-yl O-α-D-Galactopyranosyl-(1–3)-0-β-D-Galactopyranosyl-(1–4)-2-Acetamido-2-Deoxy-β-D-Glucopyranoside", Carbohy. Res., 136:207–213 (1985).

18. Garegg, P. J., et al., "Synthesis of 6- and 6'-deoxy derivatives of methyl 4-0-α-D-galactopyranosyl-β-D-galactopyranoside for studies of inhibition of pyelonephritogenic fimbriated *E. coli* adhesion to urinary epithelium-cell surfaces", Carbohy. Res., 137:270–275 (1985).

19. Jacquinet, J. C., et al., "Synthesis of Blood-group Substances, Part 11. Synthesis of the Trisaccharide O-α-D-Galactopyranosyl-(1–3)-0-β-D-galactopyranosyl-(1–4)-2-acetamido-2-deoxy-D-glucopyranose", J. C. S. Perkin, I: 326–330 (1981).

20. Koike, K., et al., "Total Synthesis of Globotriaosyl-E and Z-Ceramides and Isoglobotriaosyl-E-Ceramide," Carbohydr. Res., 163:189–208 (1987).

21. Schaubach, R., et al., "Tumor-Associated Antigen Synthesis: Synthesis of the Gal-α-(1–3)-Gal-β-(1–4)-GlcNAc Epitope. A specific Determinant for Metastatic Progression?", Liebigs Ann. Chem., 607–614 (1991).

22. Ratcliffe, R. M., et al., "Sialic Acid Glycosides, Antigens, Immunoadsorbents, and Methods for Their Preparation", U.S. Pat. No. 5,079,353, issued Jan. 7, 1992.

23. Okamoto, K., et al., "Glycosidation of Sialic Acid," Tetrahedron, 47:5835–5857 (1990).

24. Abbas, S. A., et al., "Tumor-Associated Oligosaccharides I: Synthesis of Sialyl-Lewis$^a$ Antigenic Determinant", Sialic Acids, Proc. Japan-German Symp. Berlin 22–23 (1988).

25. Paulsen, "Advances in Selective Chemical Syntheses of Complex Oligosaccharides", Angew. Chem. Int. Ed. Eng., 21:155–173 (1982).

26. Schmidt, "New Methods for the Synthesis of Glycosides and Oligosaccharides—Are There Alternatives to the Koenigs-Knorr Method?", Angew. Chem. Int. Ed. Eng., 25:212–235 (1986).

27. Fügedi, P., et al., "Thioglycosides as Glycosylating Agents in Oligosaccharide Synthesis", Glycoconjugate J., 4:97–108 (1987).

28. Kameyama, A., et al., "Total synthesis of sialyl Lewis X", Carbohydrate Res., 209: c1-c4 (1991).

29. Ekborg, G., et al., "Synthesis of Three Disaccharides for the Preparation of Immunogens bearing Immunodeterminants Known to Occur on Glycoproteins", Carbohydrate Research, 110:55–67 (1982).

30. Dahmén, J., et al., "2-Bromoethyl glycosides: applications in the synthesis of spacer-arm glycosides", Carbohydrate Research, 118:292–301 (1983).

31. Rana, S. S., et al., "Synthesis of Phenyl 2-Acetamido-2-Deoxy-3-O-α-L-Fucopyranosyl-β-D-Glucopyranoside and Related Compounds", Carbohydrate Research, 1:149–157 (1981).

32. Amvam-Zollo, P., et al., "Streptococcus pneumoniae Type XIV Polysaccharide: Synthesis of a Repeating Branched Tetrasaccharide with Dioxa-Type Spacer-Arms", Carbohydrate Research, 150:199–212 (1986).

33. Paulsen, H., "Synthese von oligosaccharid-determinanten mit amid-spacer vom typ des T-antigens", Carbohydr. Res., 104:195–219 (1982).

34. Chernyak, A. Y., et al., "A New Type of Carbohydrate-Containing Synthetic Antigen: Synthesis of Carbohydrate- Containing Polyacrylamide Copolymers having the Specificity of 0:3 and 0:4 Factors of Salmonella", Carbohydrate Research, 128:269–282 (1984).

35. Fernandez-Santana, V., et al., "Glycosides of Monoallyl Diethylene Glycol. A New type of Spacer group for Synthetic Oligosaccharides", J. Carbohydrate Chemistry, 8(3):531–537 (1989).

36. Lee, R. T., et al., "Synthesis of 3-(2-Aminoethylthio) PropylGlycosides", Carbohydrate Research, 37:193–201 (1974).

37. Armstrong, G. D., et al., "Investigation of shiga-like toxin binding to chemically synthesized oligosaccharide sequences", J. Infect. Dis., 164:1160–1167 (1991).

38. Heerze, L. D. et al., "Oligosaccharide sequences attached to an inert support(SYNSORB) as potential therapy for antibiotic-associated diarrhea and pseudomembranous colitis", J. Infect. Dis., 169:1291–1296 (1994).

39. U.S. patent application Ser. No. 08/195,009, filed Feb. 14, 1994, by Heerze, et al., for TREATMENT OF ANTIBIOTIC ASSOCIATED DIARRHEA (allowed).

40. U.S. patent application Ser. No. 08/126,645, filed Sep. 27, 1993 by Armstrong, et al., for DIAGNOSIS AND TREATMENT OF BACTERIAL DYSENTERY.

41. U.S. patent application Ser. No. 07/996,913, filed Dec. 28, 1992, by Armstrong, for DIAGNOSIS AND TREATMENT OF BACTERIAL DYSENTERY.

The disclosure of the above publications, patents and patent applications are herein incorporated by reference in their entirety to the same extent as if the language of each individual publication, patent and patent application were specifically and individually included herein.

BACKGROUND OF THE INVENTION

Cholera is a severe diarrheal disease that affects approximately 3 million individuals per year worldwide (mainly in less developed countries). It is caused by consuming food or drinking water contaminated with the microorganism *Vibrio cholerae*. When the organism is ingested, it has the ability to colonize the intestinal tract.

In the small intestine, *V. cholerae* attaches to the intestinal mucosa and releases exotoxins, the most important being cholera toxin (CT), which act on mucosal cells [1–4]. The action of CT on intestinal cells induces fluid secretion and increased permeability of electrolytes into the small intestine resulting in severe diarrhea and electrolyte imbalance.

Two other toxins are also produced by *V. cholerae*. They include zona occludens toxin (Zot) which disrupts tight junctions between cells, and accessory cholera enterotoxin (Ace), which causes diarrhea in animals. The role of these two toxins in the overall pathogenesis of the disease remains unclear.

An additional cytolytic toxin is produced by O1 El Tor and O139 serotypes of *V. cholerae*. This toxin has a hemolytic and cytotoxic activity which appears to play a role in the pathogenesis of cholera.

Mortality rates are high for infants and children that are inflicted with cholera. The current method of treatment for cholera is to replace fluids and restore electrolyte balance.

Not all strains of *V. cholerae* are responsible for causing disease. The disease causing strains belong to the O1 serotype which includes the classical and the El Tor biotypes. All other serotypes except for one are thought to be nonvirulent or capable of causing only minor diarrhea. The only non O1 strain of *V. cholerae* that has been shown to cause full-blown cholera was identified two years ago. It belongs to the O139 serotype. This serotype has been identified as the causal agent for recent outbreaks of cholera in Asia. It produces all the virulence factors (including CI) associated with the O1 serotypes of *V. cholerae*.

The virulence factors most important for causing disease are the toxin coregulated pili (Tcp) which allow *V. cholerae* to colonize the small intestine. Although the host cell receptor has yet to be identified for pili, there is some indirect evidence which suggests that a carbohydrate may be involved. This evidence is based on the finding that individuals who have the O blood group are more susceptible to severe cases of cholera while people who are AB blood group positive tend to be somewhat resistant toward the disease. One possible explanation for this finding is that the pili found on *V. cholerae* may use the O blood group oligosaccharide structure for colonization of the small intestine, thus rendering individuals with the O blood group more susceptible to disease.

CT is the virulence factor most responsible for the symptoms of the disease. CT possesses an enzymatic activity which elevates the levels of cyclic AMP (cAMP) in host cells. The increase in cAMP levels alters the ion transport systems within cells thus affecting the osmotic balance within the intestine that leads to diarrhea. CT utilizes the ganglioside GM1 ($\beta$Gal(1–3)$\beta$GalNAc(1–4)[$\alpha$NeuAc(2–3)] $\beta$Gal(1–4)$\beta$Glc-ceramide) to bind to host cell receptors.

Cholera toxin (CT) has been shown to bind to several derivatives of the ganglioside GM1 where the carboxyl group of sialic acid had been modified to form a number of C(1) amides [5]. The structure of these compounds is: $\beta$Gal(1–3) $\beta$GalNAc(1–4)[$\alpha$NeuAcR(2–3)] $\beta$Gal(1–4) $\beta$Glc-ceramide, where R is selected from the group consisting of amide, methylamide, ethylamide, propylamide, and benzylamide of sialic acid.

Other derivatives of GM1 that were shown to bind CT include [6]: $\beta$Gal(1–3) $\beta$GalNH2(1–4)[$\alpha$Neu-NH2(2–3)] $\beta$Gal(1–4)$\beta$Glc-ceramide; $\beta$Gal(1–3) $\beta$GalNAc(1–4) [$\alpha$NeuAcR(2–3)] $\beta$Gal(1–4)$\beta$Glc-ceramide, where R is the methyl ester of sialic acid; $\beta$Gal(1–3)$\beta$GalNAc(1–4)[$\alpha$(C7) NeuAc(2–3)] $\beta$Gal(1–4)$\beta$Glc-ceramide; and $\beta$Gal(1–3) $\beta$GalNAc(1–4)[$\alpha$NeuAcR(2–3)]$\beta$Gal(1–4)$\beta$Glc-ceramide, where R is ethanolamineamide.

Other gangliosides which have been shown to bind CT include[6,7]: GM2 ($\beta$GalNAc(1–4)[$\alpha$NeuAc(2–3)] $\beta$Gal (1–4)$\beta$Glc-ceramide) and GD1b ($\beta$Gal(1–3) $\beta$GalNAc(1–4) [$\alpha$NeuAc(2–3)$\alpha$NeuAc(2–3)] $\beta$Gal(1–4)$\beta$Glc-ceramide.

In addition, highly purified CT preparations have been obtained using lyso GM1 ganglioside or galactose affinity columns [8–10].

With respect to methods of diagnosis of the presence of CT in a sample, one method for detecting *Vibrio cholerae* in a sample is to culture the sample. The disadvantages of this method include the length of time required and interference by non-pathogenic, i.e., non-toxin producing, *V. cholerae* strains. Other methods involve the use of specific antisera or monoclonal antibodies.

In view of the above, there is a need for a compound which would treat cholera. A preferred compound would be administered noninvasively, such as orally, and would specifically remove toxin and/or organisms from the intestinal tract.

SUMMARY OF THE INVENTION

The invention provides compositions and methods for the treatment of cholera and associated symptoms caused by cholera toxin.

The invention also provides compositions and methods for the treatment of cholera and associated symptoms caused by colonization of the gastrointestinal tract by V. cholerae.

In one aspect, the invention provides a method to treat cholera in a subject, which method comprises administering to a subject in need of such treatment an effective amount of a composition comprising an oligosaccharide sequence covalently attached to a pharmaceutically acceptable solid, inert support through a non-peptidyl compatible linker arm, wherein said oligosaccharide sequence binds cholera toxin, and wherein said composition is capable of being eliminated from the gastrointestinal tract.

In a further aspect, the invention provides a pharmaceutical composition useful in treating cholera and related conditions initiated by cholera toxin, which composition comprises an oligosaccharide sequence covalently attached to a pharmaceutically acceptable solid, inert support through a non-peptidyl compatible linker arm, wherein said oligosaccharide sequence binds cholera toxin; and a pharmaceutically acceptable carrier, wherein said composition is capable of being eliminated from the gastrointestinal tract.

In yet a further aspect, the invention provides a method to treat cholera in a subject, which method comprises administering to a subject in need of such treatment an effective amount of a composition comprising an oligosaccharide sequence covalently attached to a pharmaceutically acceptable solid, inert support through a non-peptidyl compatible linker arm, wherein said oligosaccharide sequence binds V. cholerae, and wherein said composition is capable of binding the microorganism so that it is eliminated from the gastrointestinal tract.

In a still further aspect, the invention provides a pharmaceutical composition useful in treating cholera and related conditions, which composition comprises an oligosaccharide sequence covalently attached to a pharmaceutically acceptable solid, inert support through a non-peptidyl compatible linker arm, wherein said oligosaccharide sequence binds V. cholerae; and a pharmaceutically acceptable carrier, wherein said composition is capable of binding the microorganism so that it is eliminated from the gastrointestinal tract.

In yet a still further aspect, the invention provides a method to bind and remove cholera toxin and/or V. cholerae organisms from a sample suspected of containing said toxin or organism, which method comprises contacting said sample with an oligosaccharide sequence covalently attached to a solid, inert support through a non-peptidyl compatible linker arm, wherein said oligosaccharide sequence binds cholera toxin and/or V. cholerae organisms, under conditions wherein said cholera toxin and/or V. cholerae organism is absorbed to said support; and separating the support containing the absorbed toxin and/or organism from the sample.

BRIEF DESCRIPTION OF THE DRAWINGS

FIG. 3 demonstrates the neutralization of cholera toxin and cholera cytotoxin activity produced by O139 V. cholerae using SYNSORB 16, 41, 72, 75 and 88 at a concentration of 20 mg/ml. Several SYNSORBs were effective at neutralizing both activities.

FIG. 4 demonstrates the neutralization of cholera toxin and cholera cytotoxin activity produced by O1 (El Tor biotype) V. cholerae using SYNSORB 16, 41, 72, 75 and 88 at a concentration of 20 mg/ml. Several SYNSORBs were effective at neutralizing both activities.

FIG. 9 demonstrates the effectiveness of SYNSORB in binding O139 V. cholerae. The results show that O139 serotypes of V. cholerae bind to SYNSORBs 2, 5, 57 and 90.

DETAILED DESCRIPTION OF THE INVENTION

A. Definitions

Figure 1:
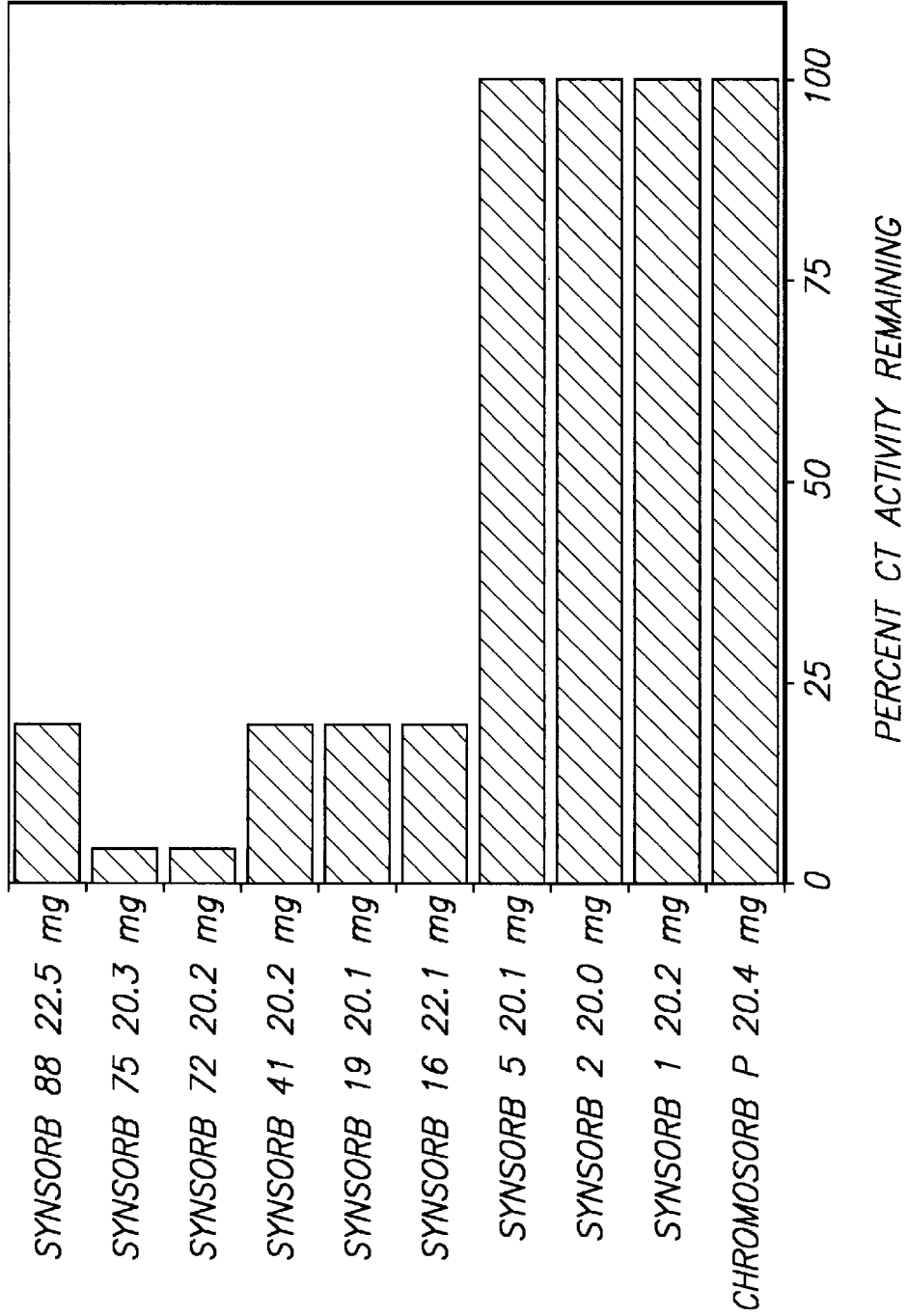
FIG. 1 demonstrates the neutralization of purified cholera toxin cytotonic activity using a panel of SYNSORBs containing various oligosaccharide sequences. Several SYNSORBs were found to effectively neutral cholera toxin activity.

As used herein the following terms have the following meanings:

The term "cholera" refers to an acute epidemic infectious disease caused by Vibrio cholerae, wherein a soluble toxin elaborated in the intestinal tract by the Vibrio alters the permeability of the mucosa, causing a profuse watery diarrhea, extreme loss of fluid and electrolytes, and a state of dehydration and circulatory collapse, but no gross morphologic change in the intestinal mucosa.

The term "biocompatible" refers to chemical inertness with respect to human tissues or body fluids. Biocompatible materials are non-sensitizing.

The term "compatible linker arm" refers to a moiety which serves to space the oligosaccharide structure from the biocompatible solid support and which is biofunctional wherein one functional group is capable of binding to a reciprocal functional group of the support and the other functional group is capable of binding to a reciprocal functional group of the oligosaccharide structure. Compatible linker arms preferred in the present invention are non-peptidyl spacer arms.

The term "solid support" refers to an inert, solid material to which the oligosaccharide sequences may be bound via a compatible linker arm. Where use is in vivo, the solid support will be biocompatible.

The term "SYNSORB" refers to synthetic 8-methoxycarbonyloctyl oligosaccharide structures covalently coupled to Chromosorb P™ (Manville Corp., Denver, Colo.) [11], which is a derivatized silica particle.

The term "cholera toxin" refers to an enterotoxin of V. cholerae which initiates cholera and related conditions. This toxin has a lectin-like activity.

For purpose of this application, all sugars are referenced using conventional three letter nomenclature. All sugars are assumed to be in the D-form unless otherwise noted, except for fucose, which is in the L-form. Further all sugars are in the pyranose form.

B. Synthesis

Chemical methods for the synthesis of oligosaccharide structures can be accomplished by methods known in the art. These materials are generally assembled using suitably protected individual monosaccharides.

The specific methods employed are generally adapted and optimized for each individual structure to be synthesized. In general, the chemical synthesis of all or part of the oligosaccharide glycosides first involves formation of a glycosidic linkage on the anomeric carbon atom of the reducing sugar or monosaccharide. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possesses one free hydroxyl group at the position where the glycosidic linkage is to be established. A large variety of aglycon moieties are known in the art and can be attached with the proper configuration to the anomeric center of the reducing unit.

Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature [12–28].

The solid supports to which the oligosaccharide structures of the present invention are bound may be in the form of sheets or particles. A large variety of biocompatible solid support materials are known in the art. Examples thereof are silica, synthetic silicates such as porous glass, biogenic silicates such as diatomaceous earth, silicate-containing minerals such as kaolinite, and synthetic polymers such as polystyrene, polypropylene, and polysaccharides. Solid supports made of inorganic materials are preferred. Preferably the solid supports have a particle size of from about 10 to 500 microns for in vivo use. In particular, particle sizes of 100 to 200 microns are preferred.

The oligosaccharide structure(s) is covalently bound or noncovalently (passively) adsorbed onto the solid support. The covalent bonding may be via reaction between functional groups on the support and the compatible linker arm of the oligosaccharide structure. It has unexpectedly been found that attachment of the oligosaccharide structure to the biocompatible solid support through a compatible linking arm provides a product which, notwithstanding the solid support, effectively removes toxin. Linking moieties that are used in indirect bonding are preferably organic bifunctional molecules of appropriate length (at least one carbon atom) which serve simply to distance the oligosaccharide structure from the surface of the solid support.

The compositions of this invention are preferably represented by the formula:

$(OLIGOSACCHARIDE\text{-}Y\text{-}R)_n$— SOLID SUPPORT where OLIGOSACCHARIDE represents an oligosaccharide group of at least 2 sugar units which group binds to cholera toxin and/or *V. cholerae,* Y is oxygen, sulfur or nitrogen, R is an aglycon linking arm of at least 1 carbon atom, SOLID SUPPORT is as defined above, and n is an integer greater than or equal to 1. Preferred aglycons are from 1 to about 10 carbon atoms. Oligosaccharide sequences containing about 2 to 10 saccharide units may be used. Sequences with about 2 to 3 saccharide units are preferred. Preferably, n is an integer such that the composition contains about 0.25 to 2.50 micromoles oligosaccharide per gram of composition.

Numerous aglycon linking arms are known in the art. For example, a linking arm comprising a para-nitrophenyl group (i.e., $—OC_6H_4NO_2$) has been disclosed [29]. At the appropriate time during synthesis, the nitro group is reduced to an amino group which can be protected as N-trifluoroacetamido. Prior to coupling to a support, the trifluoroacetamido group is removed thereby unmasking the amino group.

A linking arm containing sulfur has been disclosed [30]. Specifically, the linking arm is derived from a 2-bromoethyl group which, in a substitution reaction with thionucleophiles, has been shown to lead to linking arms possessing a variety of terminal functional groups such as $—OCH_2CH_2SCH_2CO_2CH_3$ and $—OCH_2CH_2SC_6H_4—pNH_2$. These terminal functional groups permit reaction to complementary functional groups on the solid support, thereby forming a covalent linkage to the solid support. Such reactions are well known in the art.

A 6-trifluoroacetamido-hexyl linking arm ($—O—(CH_2)_6—NHCOCF_3$) has been disclosed [31] in which the trifluoroacetamido protecting group can be removed, unmasking the primary amino group used for coupling.

Other exemplifications of known linking arms include the 7-methoxycarbonyl-3,6,dioxaheptyl linking arm [32] ($—OCH_2—CH_2)_2OCH_2CO_2CH_3$); the 2-(4-methoxycarbonylbutancarboxamido)ethyl [33] ($—OCH_2CH_2NHC(O)(CH_2)_4CO_2CH_3$); the allyl linking arm [34] ($—OCH_2CH{=}CH_2$) which, by radical co-polymerization with an appropriate monomer, leads to co-polymers; other allyl linking arms [35] are known ($—O(CH_2CH_2O)_2CH_2CH{=}CH2$). Additionally, allyl linking arms can be derivatized in the presence of 2-aminoethanethiol [36] to provide for a linking arm $—OCH_2CH_2CH_2SCH_2CH_2NH_2$. Other suitable linking arms have also been disclosed [12–14, 16, 17].

The particular linldng employed to covalently attach the oligosaccharide group to the solid support is not critical.

Preferably, the aglycon linking arm is a hydrophobic group and most preferably, the aglycon linking arm is a hydrophobic group selected from the group consisting of $—(CH_2)_8C(O)—$, $—(CH_2)_5OCH_2CH_2CH_2—$ and $—(CH_2)_8CH_2O—$.

We have found that synthetic oligosaccharide sequences covalently attached to a biocompatible solid support, e.g., Chromosorb P™ (SYNSORB) may be used to bind cholera toxin and/or *V. cholerae.* These compositions are useful to treat cholera and associated conditions. SYNSORB is particularly preferred for these compositions because it is non-toxic and resistant to mechanical and chemical deposition. In studies using rats (a widely accepted model for preclinical studies, since they are predictive of human response), SYNSORBs have been found to pass unaffected through the rat gastrointestinal tract. They were found to be eliminated completely and rapidly (99% eliminated in 72 hours) following oral administration.

Additionally, the high density of oligosaccharide moieties on SYNSORB is particularly useful for binding cholera toxin, since the toxin is thought to possess multiple oligosaccharide binding sites [2]. The high density of oligosaccharide ligands on SYNSORB is also useful for binding large numbers of *V. cholerae*.

Non-peptidyl linking arms are preferred for use as the compatible linking arms of the present invention. The use of glycopeptides is not desirable because glycopeptides contain several, often different, oligosaccharides linked to the same protein. Glycopeptides are also difficult to obtain in large amounts and require expensive and tedious purification. Likewise, the use of BSA or HSA conjugates is not desirable, for example, due to questionable stability in the gastrointestinal tract when given orally.

Covalent attachment of an oligosaccharide group containing a cholera toxin or *V. cholerae* binding unit through a non-peptidyl spacer arm to an inert solid support permits efficient binding and removal of cholera toxin and/or microorganism from a sample to be analyzed for the presence of cholera toxin and/or organism or from the intestine of a patient suffering from cholera. When the oligosaccharide is synthesized with this compatible linker arm attached (in non-derivatized form), highly pure compositions may be achieved which can be coupled to various solid supports.

C. Pharmaceutical Compositions

The methods of this invention are achieved by using pharmaceutical compositions comprising one or more oligosaccharide structures which bind cholera toxin and/or *V. cholerae* attached to a solid support.

When used for oral administration, which is preferred, these compositions may be formulated in a variety of ways. It will preferably be in liquid or semisolid form. Compositions including a liquid pharmaceutically inert carrier such as water may be considered for oral administration. Other pharmaceutically compatible liquids or semisolids, may also be used. The use of such liquids and semisolids is well known to those of skill in the art.

Compositions which may be mixed with semisolid foods such as applesauce, ice cream or pudding may also be preferred. Formulations, such as SYNSORBs, which do not have a disagreeable taste or aftertaste are preferred. A nasogastric tube may also be used to deliver the compositions directly into the stomach.

Solid compositions may also be used, and may optionally and conveniently be used in formulations containing a pharmaceutically inert carrier, including conventional solid carriers such as lactose, starch, dextrin or magnesium stearate, which are conveniently presented in tablet or capsule form. The SYNSORB itself may also be used without the addition of inert pharmaceutical carriers, particularly for use in capsule form.

Doses are selected to provide neutralization and elimination of cholera toxin and/or elimination of *V. cholerae* found in the gut of the affected patient. Preferred doses are from about 0.25 to 1.25 micromoles of oligosaccharide/kg body weight/day, more preferably about 0.5 to 1.0 micromoles of oligosaccharide/kg body weight/day. Using SYNSORB compositions, this means about 0.5 to 1.0 gram SYNSORB/kg body weight/day, which gives a concentration of SYNSORB in the gut of about 20 mg/ml. Administration is expected to be 3 or 4 times daily, for a period of one week or until clinical symptoms are resolved. The dose level and schedule of administration may vary depending on the particular oligosaccharide structure used and such factors as the age and condition of the subject. Optimal time for complete removal of cholera toxin activity was found to be about 1 hour at 37° C., using a concentration of SYNSORB of 20 mg in 1 ml sample. Similar conditions can be used to effectively bind and remove *V. cholerae* from the gut.

Administration of the oligosaccharide-containing compositions of the present invention during a period of up to seven days will be useful in treating cholera and associated conditions. Also, prophylactic administration will be useful to prevent colorization of the gut by *V. cholerae* and subsequent development of the disease.

As discussed previously, oral administration is preferred, but formulations may also be considered for other means of administration such as per rectum. The usefulness of these formulations may depend on the particular composition used and the particular subject receiving the treatment. These formulations may contain a liquid carrier that may be oily, aqueous, emulsified or contain certain solvents suitable to the mode of administration.

Compositions may be formulated in unit dose form, or in multiple or subunit doses. For the expected doses set forth previously, orally administered liquid compositions should preferably contain about 1 micromole oligosaccharide/ml.

D. Methodology

We have found that *V. cholerae* toxin may be neutralized by certain oligosaccharide sequences which bind the toxin. In particular, synthetic oligosaccharides covalently attached to solid supports via non-peptidyl compatible linker arms have been found to neutralize cholera toxin effectively. Examples of such compositions are certain SYNSORBs, which bind and neutralize cholera toxin activity.

We have also found that *V. cholerae* bind to certain oligosaccharide sequences that are covalently attached to solid supports via non-peptidyl compatible linker arms. Examples of such compositions are certain SYNSORBs, which bind *V. cholerae*, thereby preventing the organism from attaching to its host cell receptor in the intestinal tract before it is eliminated.

Figure 7:
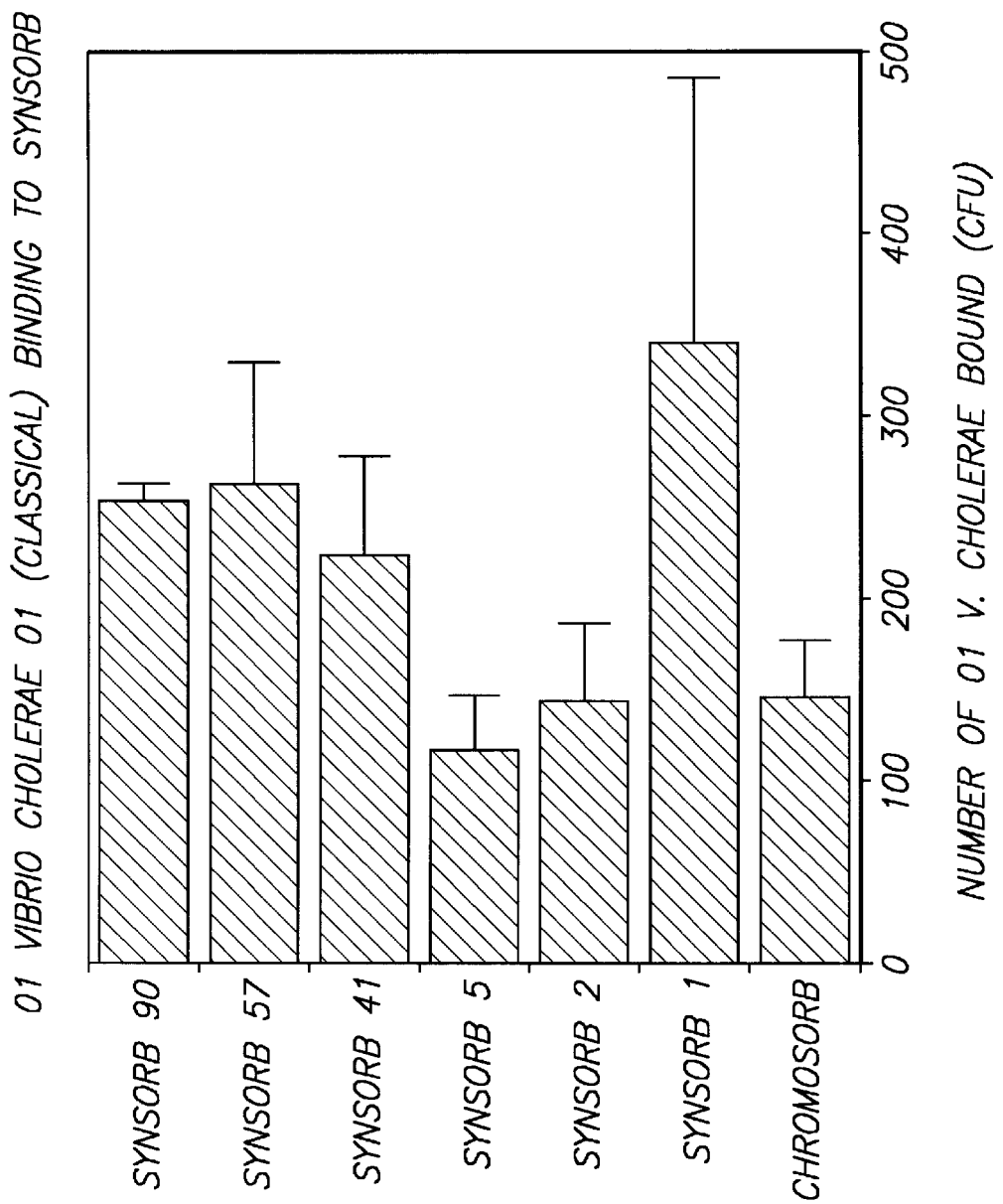
FIG. 7 demonstrates the effectiveness of SYNSORB in binding O1 V. cholerae (classical). The results show that classical biotypes of V. cholerae bind to the surface of SYNSORBs 1, 41, 57 and 90.
Figure 8:
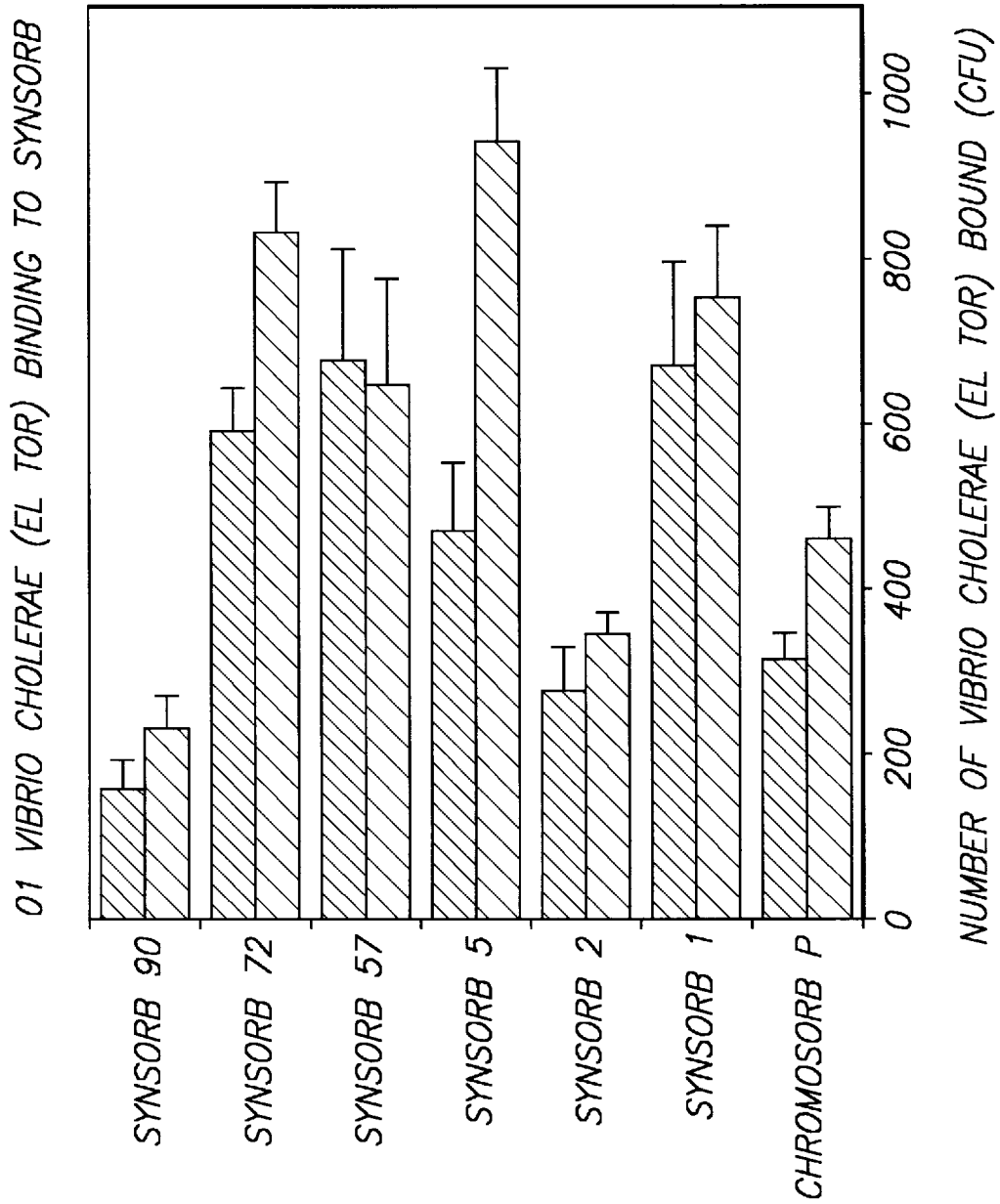
FIG. 8 demonstrates the effectiveness of SYNSORB in binding O1 V. cholerae (El Tor). The results show that El Tor biotypes of V. cholerae bind to the surface of SYNSORBs 1, 5, 57 and 72.

We have tested the ability of several oligosaccharide sequences attached to Chromosorb P via an 8-methoxylcarbonyloctyl (MCO) spacer arm to neutralize cholera toxin and bind *V. cholerae*. The structures tested, also referred to as SYNSORBs, are presented in Table 1. As shown in FIGS. 1–4, the SYNSORBs tested varied in their ability to neutralize at least about 50% of the cholera toxin activity. FIGS. 7–9 demonstrate the ability of SYNSORB to bind *V. cholerae*.

The oligosaccharide sequences attached to solid supports useful in the present invention include those which bind cholera toxin. The binding affinity of an oligosaccharide to cholera toxin is readily detectable by a simple in vitro test, as for example, set forth in Example 1 below. For the purposes of this invention, oligosaccharide sequences attached to solid supports which bind cholera toxin means those compositions which reduce endpoint titers from cytotonic activity in Chinese Hamster Ovary (CHO) cell assays by at least 50%, using the assay set forth in the Examples section.

Other oligosaccharide sequences attached to solid supports useful in the present invention are those which can bind *V. cholerae* significantly better ($p \leq 0.05$, using appropriate standard statistical methods, such as the Wilcoxon or Student's T-test) than a control support that does not contain any attached oligosaccharide sequences (e.g., Chromosorb P). The binding affinity of an oligosaccharide for V. cholerae is determined as outlined in Example 6 below.

The binding of shiga-like toxins (SLTs) and *Clostridium difficile* toxin A to chemically synthesized oligosaccharide sequences has been studied [37–41].

SLTs are a group of cytotoxins which are made up of two parts: an A subunit and a B oligomer. The B oligomer is the binding portion of the toxin that allows it to bind to host cell receptors. The SLT toxins bind to glycolipid receptors containing the αGal(1–4)βGal determinant. The A subunit has an enzymatic activity (N-glycosidase) that depurinates 28S ribosomal RNA in mammalian cells. This enzymatic activity abolishes the ability of the toxin-infected cell to perform protein synthesis.

The site for SLT action is endothelial cells found in the kidneys and mesenteric vasculature, and SLTs may cause damage that can result in renal failure and hemoglobin in the urine. SLTs are the causative agent in the hemolytic-uremic syndrome. SLTs may also be partially involved in the pathogenesis of hemorrhagic colitis (bloody diarrhea).

*Clostridium difficile* toxin A is an enterotoxin that induces fluid secretion, mucosal damage and intestinal inflammation. It serves as a chemoattractant for human neutrophils. Toxin A is a single protein. It causes activation and results in the release of cytokines in monocytes. These inflammatory effects may play an important role in inducing the colonic inflammation seen in pseudomembranous colitis.

Toxin A appears to bind to a glycoprotein receptor, the structure of which has yet to be determined. The mechanism of action is not totally understood, but toxin A is thought to enter cells via receptor-mediated endocytosis and affect the actin cytoskeleton of the cell. The toxin A receptor is thought to be linked to a guanine regulatory protein. Toxin A is the first step in the production of CDAD and PMC.

In contrast, cholera toxin is an $AB_5$ hexameric protein with five identical B subunits and one A subunit. The B-pentamer recognizes and binds to the cells of the intestine through a glycolipid receptor (ganglioside GM1). The A subunit, which is enzymatically active, is then transported to the interior of the cell, where it causes elevated levels of cyclic AMP, leading to the massive loss of fluids which characterizes cholera and related conditions.

Previous studies defining the oligosaccharide binding specificity of cholera toxin have identified several structural requirements for toxin binding [1,5–10]. The major structural requirement for cholera toxin binding is βGal(1–3)βGalNAc(1–4)[αNeuAc(2–3)]βGal [7]. Cholera toxin has also been shown to bind to galactose affinity columns, indicating that terminal galactose sugars are important for toxin binding [8]. The importance of terminal galactose sugars is also confirmed in reduced binding of cholera toxin to the ganglioside GM2 (βGalNAc(1-4)[αNeuAc(2–3)]βGal(1–4)βGlc-ceramide) [6]. Sialic acid plays a major role in cholera toxin binding [1,5]. Removal of sialic acid from GM1 to form asialo GM1 (βGal(1–3)βGalNAc(1–4)βGal(1–4)βGlc-ceramide dramatically reduces cholera toxin binding [6]. The SYNSORBs chosen for toxin neutralization studies include carbohydrates that incorporate selected segments of the GM1 oligosaccharide structure. Other additional SYNSORBs selected for binding studies contain oligosaccharide sequences that represent analogs of selected sequences in the GM1 ganglioside structure. Oligosaccharide structures comprising a terminal βGal(1–3)βGal(1–4)βGal(1) moiety are also useful in the present invention.

Figure 2:
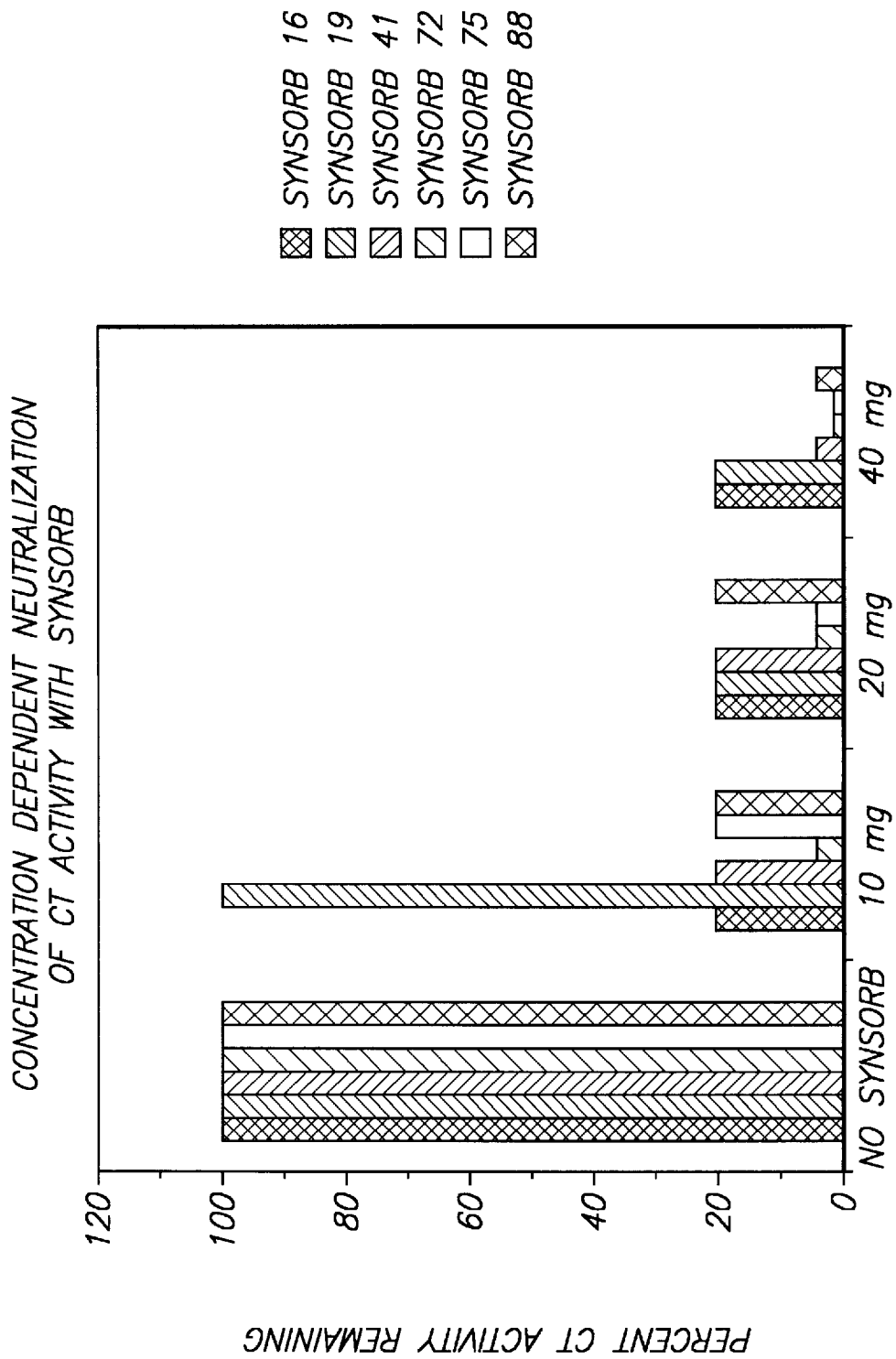
FIG. 2 illustrates the concentration dependent neutralization of cholera toxin activity using SYNSORB 16, 19, 41, 72, 75 and 88. All these SYNSORBs can effectively neutralize more than about 75% of cholera toxin activity at a concentration of 20 mg/ml.

The amount of cholera toxin adsorption to SYNSORB was determined by assaying supernatants for percent of toxin activity remaining relative to controls without any added SYNSORB. Results are shown in FIGS. 1 and 2. SYNSORBs 16, 19, 41, 72, 75 and 88 were found to effectively remove cholera toxin activity. Four of these SYNSORBs (41, 72, 75 and 88) contained oligosaccharide sequences not previously shown to bind cholera toxin.

Thus, we have found that the ability to neutralize cholera toxin is directly related to the oligosaccharide sequences attached to the inert support. The results in FIGS. 1 and 2 show the importance of the βGal(1–3)βGalNAc linkage for high affinity toxin binding. In addition, we have found that oligosaccharide sequences which possess βGal(1–3)βGalNAc(1–4)βGal and αNeuAc(2–3)βGal show high affinity toxin binding. We have further found that cholera toxin binds oligosaccharide sequences having βGal(1–3)βGal linkage. This structure represents an analog of the βGal(1–3)βGalNAc sequence found in the GM1 structure.

The results presented in FIGS. 1 and 2 show percent toxin activity remaining. These results were obtained in tissue culture assays using Chinese hamster ovary (CHO) cells that showed a reduction in endpoint dilution relative to controls when SYNSORB was added to purified cholera toxin.

Several different oligosaccharide sequences attached to solid supports via compatible linker arms have been found to have the ability to neutrae cholera toxin activity. These sequences, and others that also bind cholera toxin, may be used to treat cholera and related conditions. Optimal time for complete removal of cholera toxin activity was found to be about 1 hour at 37° C., using a concentration of SYNSORB of 20 mg in 1 ml sample. Since each gram of SYNSORB contains approximately 0.25 to 1.0 micromoles oligosaccharide, the total amount of oligosaccharide to be given in a daily dose would range from 7.5 to 30 micromoles, using a gut volume of four liters.

Figure 5:
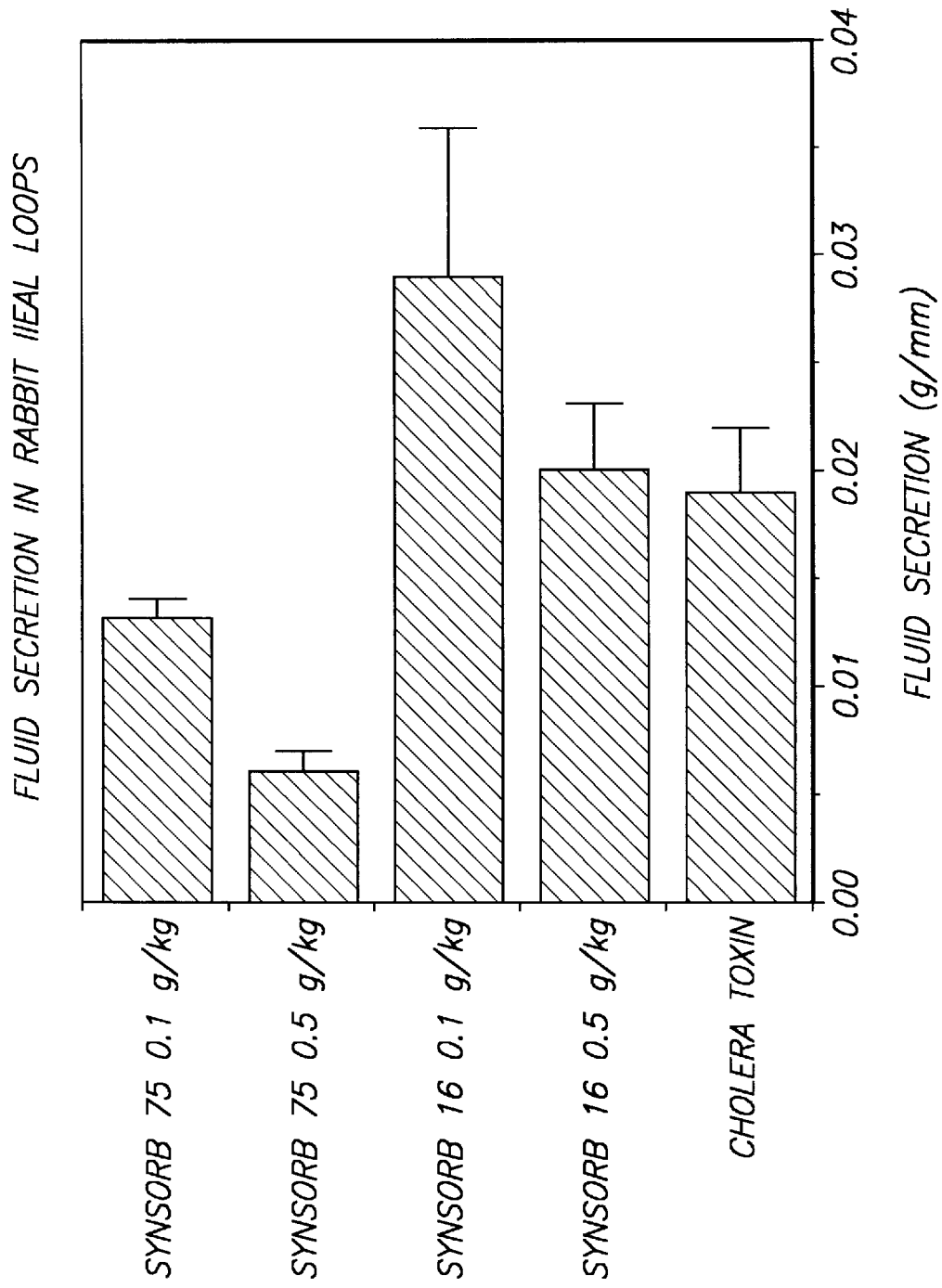
FIG. 5 illustrates the effectiveness of SYNSORBs 16 and 75 at reducing cholera toxin-mediated fluid secretion in rabbit intestinal loops. SYNSORB 75 utilized at a dose of 0.5 g/kg significantly reduced fluid secretion in rabbit intestinal loops that had been treated with purified cholera toxin.
Figure 6:
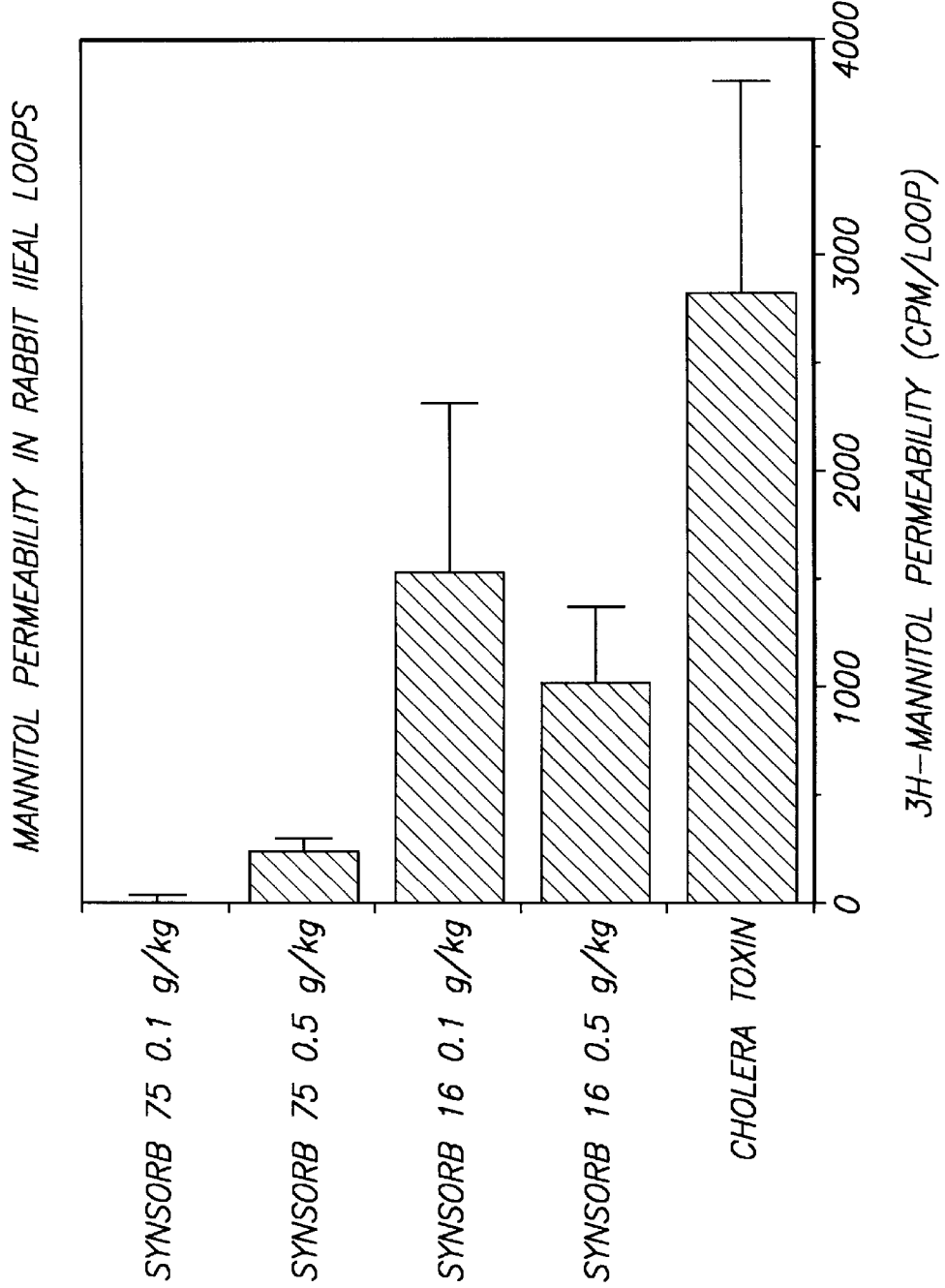
FIG. 6 illustrates the effectiveness of SYNSORBs 16 and 75 at reducing cholera toxin-mediated mannitol permeability in rabbit intestinal loops. SYNSORB 75 utilized at a dose of 0.1 g/kg and SYNSORB 16 at a dose of 0.5 g/kg significantly reduced intestinal permeability in rabbit intestinal loops that had been treated with purified cholera toxin.

The utility of oligosaccharide sequences attached to a solid support via a compatible linker arm to treat cholera was also demonstrated by the ability of SYNSORB compositions to neutralize cholera toxin in an in vivo animal model using rabbits. The results in FIGS. 5 and 6 and Table 3 show that SYNSORB 75 can effectively reduce cholera toxin-mediated fluid secretion and mannitol permeability in ligated rabbit intestinal loops. Further, the conditions used in the rabbit model best approximate the actual conditions found in the human intestine.

Treatment of cholera or related conditions may be accomplished by oral administration of compositions containing oligosaccharide sequences covalently bound to a solid support via a compatible linker arm (e.g. SYNSORBs). For example, the SYNSORB has been found to pass through the stomach of rats intact. It then contacts the cholera toxin in the intestinal tract. Subsequent elimination of the intact SYNSORB with cholera toxin bound to it results in elimination of cholera toxin from the patient.

The primary virulence factor responsible for attachment of V. *cholerae* to epithelial cells in the intestine is the toxin coregulated pili. The host cell receptors used for the attachment process have not been determined, but there is indirect evidence that suggests that attachment may be mediated by blood group oligosaccharide sequences found on epithelial cells. The SYNSORBs chosen (Table 1) for bacterial attachment studies include carbohydrates related to the A, B and O blood group structures. Additional SYNSORBs chosen contain oligosaccharide sequences that were shown to bind to cholera toxin.

The amount of *V. cholerae* binding to the surface of SYNSORB was determined by plating suspensions of SYNSORB that had been incubated with a culture of either O1 (Classical and El Tor) or O139 *V. cholerae* ($1\times10^5$ colony forming units (CFU)/ml). Control incubations were done with *V. cholerae* and Chromosorb P, which does not have any attached oligosaccharide sequences. The results in FIGS. 7–9 show that SYNSORBs 1, 2, 5, 57, 72 and 90 bind one or more serotypes of *V. cholerae*. All six of these SYNSORBs contain oligosaccharide sequences that have not been previously shown to bind *V. cholerae*. These results also confirm epidemiological evidence that suggests a relationship between blood group and an individual's susceptibility to cholera.

Thus, we have found that the ability to bind *V. cholerae* is directly related to the oligosaccharide sequences attached to the inert support. The results in FIGS. 7–9 show the importance of the αGalNAc(1–3)[αFuc(1–2)βGal (Blood group A), αGal(1–3)[αFuc(1–2)βGal (Blood group B) and αFuc(1-2)βGal(1–4)βGlcNAc (H(O) blood group) linkages for *V. cholerae* binding. In addition, we have found that oligosaccharide sequences which possess βGalNAc(1–4)βGal and βGal(1–3)βGal can also effectively bind *V. cholerae*. Accordingly, oligosaccharide sequences comprising βGal(1–4)βGal(2) will be useful in the methods and composition of the present invention.

Treatment of cholera or related conditions may be accomplished by oral administration of compositions containing oligosaccharide sequences covalently bound to a solid support via a compatible linker arm (e.g. SYNSORBs). For example, the SYNSORB has been found to pass through the stomach of rats intact. It then contacts the organism *V. cholerae* in the intestinal tract. Subsequent elimination of the intact SYNSORB with *V. cholerae* bound to it results in elimination of the organism from the patient.

Another aspect of the invention is the rapid efficient binding of physiological concentrations of cholera toxin or *V. cholerae* present in biological samples, thus permitting assay of the presence and/or quantity of cholera toxin or organism in these samples. Typically, the biological sample will be a stool sample. The sample may be extracted and prepared using standard extraction techniques. The sample or extract is then contacted with the toxin or organism binding oligosaccharide sequences covalently bound to solid supports via a compatible linker arm under conditions where any cholera toxin or *V. cholerae* in the sample is absorbed.

Cholera toxin or *V. cholerae* may be measured directly on the surface of the oligosaccharide-containing support using any suitable detection system. For example, radioactive, biotinylated or fluorescently labelled monoclonal or polyclonal antibodies specific for cholera toxin may be used to determine the amount of cholera toxin bound to the support. A wide variety of protocols for detection of formation of specific binding complexes analogous to standard immunoassay techniques is well known in the art.

A panel of SYNSORBs (Table 1) was screened for the ability to neutralize purified CT activity. The results in FIG. 1 show that SYNSORBs 16, 19, 41, 72 75 and 88 removed 80%, 80%, 80%, 96%, 96% and 80% (n=2) respectively. The SYNSORBs that bound to CT with higher affinities fit very well with data obtained from X-ray crystallographic studies which showed that the terminal disaccharide sequence (βGal(1–3)βGalNAc) as well as the sialic acid sugar from the GM1 structure played major roles in the interaction between toxin and carbohydrate [2]. The results from FIG. 1 also showed that Chromosorb P did not appear to bind to CT.

Variable amounts of each SYNSORB were incubated with purified CT in order to determine optimal binding conditions. The results from neutralization experiments (FIG. 2) showed that SYNSORB used at a concentration of 20 mg/ml should be effective at neutralizing CT activity.

To determine whether the optimized conditions were effective at adsorbing CT activity from O1 serotypes of *V. cholerae*. Crude culture supernatants from Classical and El Tor biotypes of *V. cholerae* were incubated with SYNSORBs 16, 41, 72, 75 and 88. The results from neutralization experiments with a classical biotype of O1 *V. cholerae* indicted that CT activity was reduced by 94±3%, 90±0%, 77±0%, 97±0% and 97±0% (n=4) respectively for each of the SYNSORBs listed above. Using two culture supernatants from El Tor biotypes of O1 *V. cholerae* (NIH V86 and 95-0031), SYNSORBs 16, 41, 72, 75 and 88 reduced CT activity by 81±0%, 75±0%, 89±0%, 81±0% and 75±0% (n=2) and 50±0%, 75±0%, 88±0%, 66±0% and 94±0% (n=2) respectively.

Preliminary CT neutralization experiments with four O139 *V. cholerae* clinical isolates obtained from Dr. W. Johnson, LCDC, Ottawa revealed the presence of a cytotoxic activity that is not found with the classical O1 serotypes of *V. cholerae*. Two tissue culture assays are useful for detecting CT activity. The classical CT assay involves exposing Chinese hamster ovary (CHO) cells to solutions containing toxin and determining the cytotonic (cell elongation) end point after 24 hours. The second involves HT 29 cells which produce large pleomorphic vacuoles when exposed to CT. Culture supernatants from O139 clinical isolates had the ability to rapidly kill CHO cells (100% death in less than 24 hours) and induced vacuolization in HT 29 cells (Table 2). The results from preliminary experiments indicate some differences between the O139 culture supernatants and purified CT.

To further explore the differences, neutralization experiments were done with anti-CT antiserum. Dilutions of purified CT and O139 culture supernatants were combined with anti-CT serum and incubated for 30 minutes prior to adding the toxin dilutions to CHO and HT 29 cells. After incubating with toxin for 24 hours, the results indicated that the cytotoxic activity observed with CHO cells was not neutralized by the anti-CT antiserum. Antibody neutralization experiments using HT 29 cells revealed that the antiserum effectively reduced the formation of vacuoles, suggesting the presence of CT in the culture supernatants. Control assays using purified CT showed good neutralization in both the CHO and HT 29 cells.

The data obtained from the neutralization assays suggest that two toxin activities are produced by O139 strains. One of the activities is CT, which causes vacuolization in HT 29 cells. The second activity, a cholera cytotoxin (CC) that kills CHO cells. Additional evidence to support the presence of CC in O139 culture supernatants was obtained by incubating toxin containing solutions with Vero cells which have been shown to be resistant towards the effects of CT. Incubating O139 culture supernatants with Vero cells resulted in rapid death of the cells confirming the presence an additional cytotoxic activity. El Tor biotypes of *V. cholerae* are known to possess an additional cytotoxic/hemolytic activity that is similar to CC produced by O139 serotypes.

Preliminary neutralization studies with SYNSORBs 16, 41, 72, 75 and 88 have shown that SYNSORB has the ability to adsorb CC and CT from culture supernatants. The extent of CC neutralization was determined by comparing the cytotoxic end points of SYNSORB treated culture supernatants with untreated control samples using CHO cells. CT neutralization experiments were done in a similar manner except that HT 29 cells were used to assess toxin levels. The results in FIG. 3 show that SYNSORBs 16, 41, 72, 75 and 88 had the ability to neutralize greater than 50% of CT activity in most cases. The results also show that the cytotoxic activity produced by O139 serotypes and O1 El Tor biotypes may utilize oligosaccharide receptors similar to those used by CT for interacting with host cells. The ability of SYNSORB to neutralize CT activity from O139 V. cholerae strains was somewhat reduced when compared to the results obtained with the O1 serotype. The reduced affinities for the various SYNSORBs may be due to slight differences between the two CT activities.

E. Examples

The following methods were used to perform the studies in the Examples that follow.

Purified cholera toxin was obtained from Sigma Chemicals.

Preparation of Vibrio cholerae Culture Supernatants

*V. cholerae* O1 classical as well as El Tor biotypes were cultured in AKI media (15 g peptone (Difco), 5 g NaCl, 4 g yeast extract (Difco) per liter water, adjusted to pH 7 with sodium bicarbonate) at 37° C. while clinical isolates of *V. cholerae* O139 were grown in Syncase media (20 g casamino acids (Difco), 8.7 g $K_2HPO_4$, 6 g yeast extract (Difco), 25 g NaCl per liter water). Overnight cultures of *V. cholerae* were centrifuged at 5,000×g for 30 min. to sediment the bacteria. The supernatants were carefully removed and utilized in toxin neutralization studies.

Assay of Cholera Toxin Activity Using Tissue Culture Cells

The cytotonic activity of cholera toxin (CT) can be measured by the use of Chinese hamster ovary (CHO) cells that are maintained in Hams F12 media supplemented with 10% fetal bovine serum (FBS) in an atmosphere of 5% $CO_2$ at 37° C. CT samples to be tested were diluted 1:5 in Hams media and filter sterilized through 0.22 micron syringe filters. Samples to be tested were serial 5-fold diluted in media and 100 μL of each dilution was added to wells with confluent monolayers of CHO cells and incubated for 24 h at 37° C. in 5% $CO_2$. Each sample was analyzed two times. Cytotonic effects were readily visible after 24 h incubation by comparing wells with controls that do not contain toxin. After 24 h, the cells were fixed with 95% methanol and stained with Geimsa stain.

CT-containing samples from neutralization experiments were treated in an analogous fashion except that the percent neutralization was determined by comparing the endpoint dilutions of samples with and without SYNSORB.

Another cell line used to measure the effects of CT are human colonic adenocarcinoma HT 29 cells which are grown in the presence of 17 mM glucose using Dulbecco's Modified Eagles Medium (DMEM) plus 10% fetal bovine serum. CT containing solutions were serial 3 or 5-fold diluted in media and added to wells containing HT 29 cells. Pleomorphic vacuole formation was readily visible after 24 h incubation by comparing sample wells with controls that did not contain any toxin.

Kidney cells from the African green monkey (VERO) were used as a control cell line since they are resistant towards the effects of CT. VERO cells were maintained in minimum essential medium (MEM) containing 3% FBS.

Assay of Cholera Cytotoxin Activity Using Tissue Culture Cells

Cholera cytotoxin activity was measured in an identical manner as described above using either CHO or Vero cells.

The following examples are offered to illustrate this invention and are not meant to be construed in any way as limiting the scope of this invention.

Example 1

Screening of Oligosaccharide-containing Solid Supports for the Ability to Neutralize Cholera Toxin Activity A solution containing purified CT (2 μg in 1 ml PBS) was added to various SYNSORBs (amounts ranging from 20.0 to 22.5 mg) containing different oligosaccharide sequences in 1.5 ml microcentrifuge tubes and incubated at room temperature for 1 h on a end-over-end rotator. After incubation, the SYNSORB was allowed to settle to the bottom of the tubes and the supernatants were carefully removed. Serial five-fold dilutions of the supernatants were prepared and the cytotonic endpoint determined as described above. The extent of reduction in the endpoint in the presence of SYNSORB was determined by comparing with controls in which SYNSORB was not added. An additional control utilized was Chromosorb which is void of any carbohydrate ligand.

Results are shown in FIG. 1, and demonstrate that several oligosaccharide structures were found to effectively neutralize cholera toxin activity.

Example 2

Concentration Dependent Neutralization of Cholera Toxin Activity Using SYNSORB 16, 19, 41, 72. 75 and 88

The amount of SYNSORBs 16, 19, 41, 72, 75 and 88 required for maximal cholera toxin neutralization was determined by adding 1 ml of a purified cholera toxin solution containing 2 μg cholera toxin (CT) to pre-weighed amounts of each SYNSORB in 1.5 ml microcentrifuge tubes. SYNSORB samples were tested using 10, 20 and 40 mg amounts. Samples were incubated for 1 hour at 37° C. on an end-over-end rotator. Control samples containing only cholera toxin solution were also tested.

The amount of neutralization in each sample was determined by comparing the endpoint titers of CHO cell assays from samples with and without SYNSORB. The results, shown in FIG. 2, demonstrate that about 20 mg of each SYNSORB tested was able to neutralize at least 75% of the cholera toxin in 1 ml of cholera toxin solution.

Example 3

Characterization of Cholera Cytotoxin Produced by O139 and O1 (El Tor) Biotypes of V. cholerae

Anti-Cholera Toxin Neutralization Assays

Neutralization experiments were done with CHO or HT 29 tissue culture cells. Dilutions of culture supernatants of *V. cholerae* clinical isolates were prepared and incubated with rabbit anti-CT antiserum (diluted 100 and 1000 times in each CT dilution) for 30 minutes at 37° C. Neutralization was determined by comparing end point dilution titers of supernatants that were treated with antiserum to titers of untreated samples. All experiments were done in duplicate.

The results in Table 2 show that the cytotoxic activity produced by O139 clinical isolates was similar to the cytotoxin activity produced by O1 El Tor biotypes of *V. cholerae*. The results in FIG. 4 also show that two toxins are present in El Tor biotypes of *V. cholerae*.

Example 4

Screening of Oligosaccharide-containing Solid Supports for the Ability to Neutralize Cholera Toxin and Cholera Cytotoxin Activities from O139 and O1 El Tor Biotypes of *V. cholerae*

Crude culture supernatants from O139 and O1 El Tor biotypes of *V. cholerae* (1 ml) were added to various SYNSORBs (amounts ranging from 20.0 to 22.5 mg) containing different oligosaccharide sequences in 1.5 ml microcentrifuge tubes and incubated at room temperature for 1 h on a end-over-end rotator. After incubation, the SYNSORB was allowed to settle to the bottom of the tubes and the supernatants were carefully removed. Serial three or five-fold dilutions of the supernatants were prepared and the cytotonic or cytotoxic endpoints determined as described above. The extent of reduction in the endpoint in the presence of SYNSORB was determined by comparing with controls in which SYNSORB was not added. An additional control utilized was Chromosorb which is void of any carbohydrate ligand.

Results are shown in FIGS. 3 and 4, and demonstrates the neutralization of cholera cytotoxin and cholera toxin activity using SYNSORBs at a concentration of 20 mg/ml. The results in FIGS. 3 and 4 indicate that several oligosaccharide structures were found to effectively neutralize both toxin activities.

Example 5

Determination of the Efficacy of SYNSORB in Reducing the Effects of Cholera Toxin in the Small Intestine of Rabbits Specific pathogen free (SPF) male New Zealand white rabbits weighing approximately 2 kg were used to assess the potential of SYNSORB to reduce the effects of CT in the ileum. Prior to surgery, each rabbit was fasted but provided with water ad libitum. Rabbits were then anesthetized by administering Isoflorane by means of a face mask. Using sterile techniques, the abdomen was opened along the midsection and four to six 10 cm long segments of ileum were ligated with umbilical tape to form loops. Each loop was separated by a 5 cm intestinal segment. To each loop was added 1.5 ml of a suspension of either SYNSORB 16 or 75 at a specified dose (0.1 lg/kg or 0.5g/kg) in 6 ml of 0.5% carboxymethyl cellulose. Each intestinal loop of control animals received only 1.5 ml of 0.5 % carboxymethyl cellulose.

Prior to addition of purified CT to the intestinal loops, ten $\mu$Ci of $^3$H-mannitol (100 $\mu$L) was injected intravenously into the ear vein of each rabbit by syringe. Each intestinal loop was then injected with either 100 $\mu$L of a CT solution (25 $\mu$g) or phosphate buffered saline by tuberculin syringe. The intestinal loops were then replaced in the abdomen and the incision closed. Each rabbit was maintained under light Isoflorane anesthesia for 4 hours, maintaining body temperature constant at 37° C. by placing each rabbit on a water circulating heating pad for the duration of the experiment. At the termination of the incubation period, rabbits were then sacrificed by an intravenous injection of pentobarbital. The ileal loops were removed, weighed and their lengths measured. The loop contents were carefully removed and assayed for loop volume as well as the amount of $^3$H-mannitol in each loop.

The results from our studies (FIGS. 5 and 6, Table 3) show that SYNSORB 75 was effective at minimizing CT activity in the intestines of rabbits.

Example 6

Binding Experiments Using SYNSORB and *Vibrio cholerae*

Binding experiments were done by incubating approximately $10^5$ CFU of O1 *V. cholerae* (Classical and El Tor biotypes) or O139 *V cholerae* in 0.5 ml of PBS with SYNSORBs 1, 2, 5, 57, 72 or 90 and Chromosorb P (20 mg) for 30 min. at room temperature. After extensive washing of the SYNSORB with PBS (about 20 ml) to remove non adherent organisms, the SYNSORB was suspended in 1 ml of 0.5% (w/v) carboxymethyl cellulose and two dilutions of the suspension were plated on nutrient agar plates. After 24 h the plates were counted to determine the number of bound Vibrios. The results in FIGS. 7–9 show that *V. cholerae* can effectively bind to the surface of SYNSORB. The results also indicate that several oligosaccharide structures were found to effectively serve as binding sites for *V. cholerae*. The binding to SYNSORB is related to the oligosaccharide sequences found on SYNSORB since there is a significant difference between organism binding to SYNSORB and Chromosorb P alone. The results in FIGS. 7–9 represent an average of at least 4 determinations.

Modification of the above-described modes of carrying out various embodiments of this invention will be apparent to those skilled in the art following the teachings of this invention as set forth herein. The examples described above are not limiting, but are merely exemplary of this invention, the scope of which is defined by the following claims.

TABLE 1

SYNSORBs Used in Cholera Toxin Neutralization Studies

| SYNSORB Number | Structure Number | Common Name | Oligosaccharide Structure* |
|---|---|---|---|
| 1 | 1 | A | $\alpha$GalNAc (1–3) $\beta$Gal (1–2) $\alpha$Fuc |
| 2 | 2 | B | $\alpha$Gal (1–3) $\beta$Gal (1–2) $\alpha$Fuc |
| 5 | 3 | H Type 2 | $\beta$Gal (1–4) $\beta$GlcNAc (1–2) $\alpha$Fuc |
| 16 | 4 | lactose | $\beta$Gal (1–4) $\beta$Glc |
| 19 | 5 | — | $\beta$Gal |
| 41 | 6 | — | $\beta$Gal (1–3) $\beta$GalNAc |
| 57 | 7 | — | $\beta$GalNAc (1–4) $\beta$Gal |
| 75 | 8 | — | $\beta$Gal (1–3) $\beta$GalNAc (1–4) $\beta$Gal |
| 88 | 9 | — | $\alpha$NeuAc (2–3) $\beta$Gal |
| 72 | 10 | — | $\beta$Gal (1–3) $\beta$Gal |
| 90 | 11 | — | $\alpha$Gal (1–3) $\beta$Gal (1–4) $\beta$Glc |

*All oligosaccharides are linked to Chromosorb P through a hydrophobic 8 carbon spacer arm. NeuAc is the abbreviation for sialic acid.

TABLE 2

Effects of Culture Supernatants from *V. cholerae* O1 and O139 on Tissue Culture Cells*

| Serotype | CHO Cells | Anti-CT Neutralization (CHO Cells) | HT 29 Cells | Anti-CT Neutralization (HT 29 Cells) | Vero Cells |
|---|---|---|---|---|---|
| Purified CT | cytotonic | yes | vacuolization | yes | no effect |
| O1 (Inaba) | cytotonic | yes | vacuolization | yes | no effect |
| O139-93-302 | cytotoxic | no | vacuolization | yes | cytotoxic |
| O139-93-329 | cytotoxic | no | vacuolization | yes | cytotoxic |
| O139-93-520 | cytotoxic | no | vacuolization | yes | cytotoxic |
| O139-93-695 | cytotoxic | no | vacuolization | yes | cytotoxic |
| O1 E1 Tor NIH V86 | cytotoxic | no | vacuolization | yes | N.D. |
| O1 E1 Tor 95-0031 | cytotoxic | no | vacuolization | yes | N.D. |

*Neutralization experiments were done with Chinese hamster ovary (CHO) or human colonic adenocarcinoma (HT 29) tissue culture cells. Dilutions of culture supernatants of *V. cholerae* clinical isolates were prepared and incubated with anti-CT for 30 minutes at 37° C. Neutralization was determined by comparing end point dilution titres of supernatants that were treated with antiserum with untreated samples. All experiments were done in duplicate.
N.D. not done.

TABLE 3

Neutralization of the Effects of CT in Ligated Rabbit Ileal Loops

| | Fluid Secretion (g/mm loop) | p* | p+ |
|---|---|---|---|
| Cholera Toxin (n = 10) | 0.019 ± 0.003 | — | — |
| CT + SYNSORB 75, 0.5 g/kg (n = 7) | 0.006 ± 0.001 | 0.018 | <0.001 |
| CT + SYNSORB 75, 0.1 g/kg (n = 4) | 0.013 + 0.001 | 0.465 | 0.380 |
| CT + SYNSORB 16, 0.5 g/kg (n = 7) | 0.020 + 0.003 | 0.735 | 0.828 |
| CT + SYNSORB 16, 0.1 g/kg (n = 4) | 0.029 + 0.007 | 1.000 | 0.692 |

| | Fluid Volume (ml) | p* | p+ |
|---|---|---|---|
| Cholera Toxin (n = 10) | 3.46 ± 0.57 | — | — |
| CT + SYNSORB 75, 0.5 g/kg (n = 7) | 1.08 ± 0.38 | 0.018 | <0.001 |
| CT + SYNSORB 75, 0.1 g/kg (n = 4) | 2.18 ± 0.68 | 0.068 | 0.045 |
| CT + SYNSORB 16, 0.5 g/kg (n = 7) | 3.26 ± 0.55 | 0.612 | 0.549 |
| CT + SYNSORB 16, 0.1 g/kg (n = 4) | 3.70 ± 1.14 | 1.000 | 0.954 |

| | $^3$H-Mannitol Permeability (cpm loop) | p* | p+ |
|---|---|---|---|
| Cholera Toxin (n = 10) | 2821 + 984 | — | — |
| CT + SYNSORB 75, 0.5 g/kg (n = 7) | 234 ± 55 | 0.109 | 0.122 |
| CT + SYNSORB 75, 0.1 g/kg (n = 4) | 0 + 31 | 0.068 | 0.023 |
| CT + SYNSORB 16, 0.5 g/kg (n = 7) | 1024 ± 355 | 0.068 | 0.029 |
| CT + SYNSORB 16, 0.1 g/kg (n = 4) | 1529 ± 782 | 0.593 | 0.602 |

*The P values shown indicate the significance of any differences between the degree of either fluid secretion, fluid volume or mannitol permeability in SYNSORB treated rabbit ileal loops and untreated ileal loops. The P values were determined using the nonparametric Wilcoxon test on SYSTAT computer software.
+The P values were determined using the Students T test on SYSTAT computer software.

What is claimed is:

1. A method to treat cholera in a subject, which method comprises administering to a subject in need of such treatment an effective amount of a composition comprising an oligosaccharide sequence covalently attached to a pharmaceutically acceptable solid, inert support through a non-peptidyl compatible linker arm, wherein said oligosaccharide sequence binds cholera toxin, and wherein said composition is capable of being eliminated from the gastrointestinal tract.

2. The method of claim 1 wherein said oligosaccharide sequence has from 2 to 3 saccharide units.

3. The method of claim 1 wherein said oligosaccharide sequence is selected from the group consisting of the oligosaccharide structures numbers 6, 8, 9 and 10 set forth in Table 1.

4. The method of claim 1 wherein said oligosaccharide sequence covalently attached to a pharmaceutically acceptable solid, inert support through a non-peptidyl compatible linker arm is selected from the group consisting of the SYNSORBs numbers 41, 72, 75 and 88 set forth in Table 1.

5. The method of claim 1 wherein said linker arm is —$(CH_2)_8C(O)$—.

6. A method to bind and remove cholera toxin from a sample suspected of containing said cholera toxin, which method comprises:

a) contacting said sample with an oligosaccharide sequence covalently attached to a solid, inert support through a non-peptidyl compatible linker arm, wherein said oligosaccharide sequence binds cholera toxin, under conditions wherein said cholera toxin is absorbed to said support; and b) separating the support containing the absorbed cholera toxin from the sample.

7. The method of claim 6 wherein said oligosaccharide sequence has from 2 to 3 saccharide units.

8. The method of claim 6 wherein said oligosaccharide sequence is selected from the group consisting of the oligosaccharide structures numbers 6, 8, 9 and 10 set forth in Table 1.

9. The method of claim 6 wherein said oligosaccharide sequence covalently attached to a solid, inert support through a non-peptidyl compatible linker arm is selected from the group consisting of the SYNSORBs numbers 41, 72, 75 and 88 set forth in Table 1.

10. The method of claim 6 wherein said linker arm is —$(CH_2)_8C(O)$—.

11. A method to treat conditions mediated by colonization of the gastrointestinal tract by *V. cholerae* toxin in a subject, which method comprises administering to a subject in need of such treatment an effective amount of a composition comprising an oligosaccharide sequence covalently attached to a pharmaceutically acceptable solid, inert support through a non-peptidyl compatible linker arm, wherein said oligosaccharide sequence binds the *V. cholerae* toxin, and wherein said composition is capable of being eliminated from the gastrointestinal tract.

12. The method of claim 11 wherein said oligosaccharide sequence has from 2 to 3 saccharide units.

13. The method of claim 11 wherein said oligosaccharide sequence is selected from the group consisting of the oligosaccharide structures numbers 6, 8, 9 and 10 set forth in Table 1.

14. The method of claim 11 wherein said oligosaccharide sequence covalently attached to a pharmaceutically acceptable solid, inert support through a non-peptidyl compatible linker arm is selected from the group consisting of the SYNSORBs numbers 41, 72, 75 and 88 set forth in Table 1.

15. The method of claim 11 wherein said linker arm is —$(CH_2)_8C(O)$—.

* * * * *